US009561335B2

(12) United States Patent
Barish et al.

(10) Patent No.: US 9,561,335 B2
(45) Date of Patent: Feb. 7, 2017

(54) SYSTEM, DEVICE, AND METHOD FOR PROVIDING AND CONTROLLING THE SUPPLY OF A DISTENDING MEDIA FOR CT COLONOGRAPHY

(75) Inventors: Allyson Barish, Centerport, NY (US); Jeffrey B. Cushner, Woodmere, NY (US); Christopher R. Stebbins, Huntington Station, NY (US)

(73) Assignee: Bracco Diagnostics Inc., Monroe Township, NJ (US)

( * ) Notice: Subject to any disclaimer, the term of this patent is extended or adjusted under 35 U.S.C. 154(b) by 9 days.

(21) Appl. No.: 13/302,484

(22) Filed: Nov. 22, 2011

(65) Prior Publication Data

US 2012/0130304 A1    May 24, 2012

Related U.S. Application Data

(60) Provisional application No. 61/417,017, filed on Nov. 24, 2010, provisional application No. 61/499,321, filed on Jun. 21, 2011.

(51) Int. Cl.
*A61M 13/00* (2006.01)
*A61B 6/00* (2006.01)

(52) U.S. Cl.
CPC ............ *A61M 13/003* (2013.01); *A61B 6/548* (2013.01); *A61M 2202/0225* (2013.01);
(Continued)

(58) Field of Classification Search
CPC .. A61M 13/00; A61M 13/003; A61M 13/006; A61M 2205/3331; A61M 5/172; A61M 5/16804; A61M 5/16831; A61M 2205/502
(Continued)

(56) References Cited

U.S. PATENT DOCUMENTS 2,539,189 A    1/1951 Garrett
3,177,871 A    4/1965 Meyers
(Continued)

FOREIGN PATENT DOCUMENTS

CN    10 1312763 A    11/2008
CN    10 1370420 A    2/2009
(Continued)

OTHER PUBLICATIONS

International Search Report and Written Opinion for Application No. PCT/US2011/061824 dated Feb. 9, 2012.
(Continued)

*Primary Examiner* — Bhisma Mehta
*Assistant Examiner* — Jenna Zhang
(74) *Attorney, Agent, or Firm* — Alston & Bird LLP

(57) ABSTRACT

Embodiments of the present invention relate to systems, devices, and methods for delivering distending media to an organ of a patient with a dispensing device for acquiring an image of the organ while distended. In one embodiment, an insufflating device comprises a controller for detecting a pressure level of the distending media within an organ of a patient, wherein the controller is configured to signal an operator to acquire an image of the organ when the pressure level is within a predetermined pressure range for a predetermined period of time. Further, the insufflating device comprises a valve assembly in communication with the controller and in fluid communication between the source of distending media and the organ of the patient, wherein the valve assembly is configured to adjust a flow rate of the distending media delivered to the organ of the patient.

22 Claims, 13 Drawing Sheets

(52) U.S. Cl.
CPC .............. *A61M 2205/3331* (2013.01); *A61M 2205/502* (2013.01); *A61M 2205/7518* (2013.01); *A61M 2205/7536* (2013.01); *A61M 2205/8225* (2013.01)

(58) Field of Classification Search
USPC .......................................... 604/24, 506, 246
See application file for complete search history.

(56) References Cited

U.S. PATENT DOCUMENTS

| | | |
|---|---|---|
| 3,374,762 A | 3/1968 | Baldwin |
| 3,674,010 A | 7/1972 | Falenks |
| 3,858,572 A | 1/1975 | Binard et al. |
| 3,867,941 A | 2/1975 | Lindemann |
| 3,870,072 A | 3/1975 | Lindemann |
| 3,940,237 A | 2/1976 | Gonzalez et al. |
| 3,943,938 A | 3/1976 | Wexler et al. |
| 3,982,533 A | 9/1976 | Wiest |
| 4,013,076 A | 3/1977 | Puderbaugh et al. |
| 4,019,515 A | 4/1977 | Kornblum et al. |
| 4,030,500 A | 6/1977 | Ronnquist |
| 4,048,992 A | 9/1977 | Lindemann et al. |
| 4,052,986 A | 10/1977 | Scaife |
| 4,090,502 A | 5/1978 | Tajika |
| 4,117,847 A | 10/1978 | Clayton |
| 4,182,332 A | 1/1980 | Delaney |
| 4,207,887 A | 6/1980 | Hiltebrandt et al. |
| 4,260,496 A | 4/1981 | Beer |
| 4,276,874 A | 7/1981 | Wolvek et al. |
| 4,391,280 A | 7/1983 | Miller |
| 4,419,099 A | 12/1983 | Miller |
| 4,429,693 A | 2/1984 | Blake et al. |
| 4,448,207 A | 5/1984 | Parrish |
| 4,464,169 A * | 8/1984 | Semm .................. A61M 13/003 604/26 |
| 4,504,270 A | 3/1985 | Miller |
| 4,554,078 A | 11/1985 | Huggins et al. |
| 4,637,814 A | 1/1987 | Leiboff |
| 4,664,114 A | 5/1987 | Ghodsian |
| 4,676,774 A | 6/1987 | Semm et al. |
| 4,682,979 A | 7/1987 | Girouard |
| 4,687,002 A | 8/1987 | Lahr |
| 4,734,109 A | 3/1988 | Cox |
| 4,758,221 A | 7/1988 | Jureidini |
| 4,795,429 A | 1/1989 | Feldstein |
| 4,865,018 A | 9/1989 | Kanno et al. |
| 4,874,362 A | 10/1989 | Wiest et al. |
| 4,875,899 A | 10/1989 | Holtermann |
| 4,883,462 A | 11/1989 | Williamson et al. |
| 4,902,484 A | 2/1990 | Martin et al. |
| 4,917,692 A | 4/1990 | Steer et al. |
| 4,930,997 A | 6/1990 | Bennett |
| 4,946,720 A | 8/1990 | Oishi et al. |
| 4,957,486 A | 9/1990 | Davis |
| 4,971,034 A | 11/1990 | Doi et al. |
| 5,006,109 A | 4/1991 | Douglas et al. |
| 5,019,059 A | 5/1991 | Goldberg et al. |
| 5,029,580 A | 7/1991 | Radford et al. |
| 5,061,239 A | 10/1991 | Shiels |
| 5,084,060 A | 1/1992 | Freund et al. |
| 5,098,375 A | 3/1992 | Baier |
| 5,102,416 A | 4/1992 | Rock |
| 5,131,906 A | 7/1992 | Chen |
| 5,160,325 A | 11/1992 | Nichols et al. |
| 5,176,629 A | 1/1993 | Kullas et al. |
| 5,176,630 A | 1/1993 | Shilling et al. |
| 5,178,606 A | 1/1993 | Ognier et al. |
| 5,184,074 A | 2/1993 | Arakawa et al. |
| 5,196,244 A | 3/1993 | Beck |
| 5,292,304 A | 3/1994 | Mantell et al. |
| 5,312,343 A | 5/1994 | Krog et al. |
| 5,322,070 A | 6/1994 | Goodman et al. |
| 5,328,458 A | 7/1994 | Sekino et al. |
| 5,330,486 A | 7/1994 | Wilk |
| 5,360,396 A | 11/1994 | Chan |
| 5,364,363 A | 11/1994 | Pearson et al. |
| 5,365,928 A | 11/1994 | Rhinehart et al. |
| 5,382,229 A | 1/1995 | Grabenkort et al. |
| 5,383,456 A | 1/1995 | Arnold et al. |
| 5,405,319 A | 4/1995 | Abell et al. |
| 5,411,474 A | 5/1995 | Ott et al. |
| 5,423,741 A | 6/1995 | Frank |
| 5,439,441 A | 8/1995 | Grimsley et al. |
| 5,487,376 A | 1/1996 | Yabe et al. |
| 5,549,546 A * | 8/1996 | Schneider .......... A61M 13/003 604/23 |
| 5,569,216 A | 10/1996 | Kim |
| 5,676,155 A | 10/1997 | Novak et al. |
| 5,678,568 A | 10/1997 | Uchikubo et al. |
| 5,688,256 A | 11/1997 | Surratt et al. |
| 5,720,717 A | 2/1998 | D'Andrea |
| 5,779,662 A | 7/1998 | Berman |
| 5,788,688 A | 8/1998 | Bauer et al. |
| 5,800,381 A | 9/1998 | Ognier |
| 5,800,493 A | 9/1998 | Stevens et al. |
| 5,817,124 A | 10/1998 | Karell |
| 5,897,525 A | 4/1999 | Dey et al. |
| 5,978,697 A | 11/1999 | Maytal et al. |
| 5,992,419 A | 11/1999 | Sterzer et al. |
| 6,004,509 A | 12/1999 | Dey et al. |
| 6,026,684 A | 2/2000 | Calder |
| 6,059,717 A | 5/2000 | Dabney |
| 6,066,139 A | 5/2000 | Ryan et al. |
| 6,068,609 A | 5/2000 | Ott et al. |
| 6,083,162 A | 7/2000 | Vining |
| 6,136,292 A | 10/2000 | Pettersson et al. |
| RE36,994 E | 12/2000 | Anderberg |
| 6,193,649 B1 | 2/2001 | Takami et al. |
| 6,228,048 B1 | 5/2001 | Robbins |
| 6,261,227 B1 | 7/2001 | Takahashi et al. |
| 6,272,366 B1 | 8/2001 | Vining |
| 6,299,592 B1 | 10/2001 | Zander |
| 6,315,716 B1 | 11/2001 | Takami |
| 6,328,690 B1 | 12/2001 | Takami et al. |
| 6,400,157 B1 | 6/2002 | Bonanni et al. |
| 6,402,688 B1 | 6/2002 | Takami et al. |
| 6,402,714 B1 | 6/2002 | Kraft-Kivikoski |
| 6,407,308 B1 | 6/2002 | Roe et al. |
| 6,433,939 B2 | 8/2002 | Enomoto |
| 6,458,093 B1 | 10/2002 | Gord et al. |
| 6,467,775 B1 | 10/2002 | Denzinger |
| 6,471,638 B1 | 10/2002 | Chang et al. |
| 6,473,943 B1 | 11/2002 | Thacker |
| 6,478,782 B1 | 11/2002 | Wada |
| 6,485,412 B1 | 11/2002 | Byrne |
| 6,554,780 B1 | 4/2003 | Sampson et al. |
| 6,563,633 B2 | 5/2003 | Nakamura et al. |
| 6,632,194 B1 | 10/2003 | Mehner et al. |
| 6,682,479 B1 | 1/2004 | Takahashi et al. |
| 6,824,539 B2 | 11/2004 | Novak |
| 6,866,654 B2 | 3/2005 | Callan et al. |
| 6,950,691 B2 | 9/2005 | Uchikubo |
| 6,975,968 B2 | 12/2005 | Nakamitsu et al. |
| 7,035,681 B2 | 4/2006 | Johnson et al. |
| 7,063,670 B2 | 6/2006 | Sampson et al. |
| 7,066,173 B2 | 6/2006 | Banner et al. |
| 7,147,627 B2 | 12/2006 | Kim et al. |
| 7,148,887 B2 | 12/2006 | Kaufman et al. |
| 7,149,564 B2 | 12/2006 | Vining et al. |
| 7,250,035 B1 | 7/2007 | Ott et al. |
| 7,272,430 B2 | 9/2007 | Uchikubo |
| 7,320,599 B2 | 1/2008 | Morris |
| 7,361,170 B2 | 4/2008 | Williams et al. |
| 7,476,213 B2 | 1/2009 | Uesugi et al. |
| 7,485,114 B2 | 2/2009 | Stiller et al. |
| 7,485,115 B2 | 2/2009 | Nakamura |
| 7,549,421 B2 | 6/2009 | Levi et al. |
| 7,569,027 B2 | 8/2009 | Uesugi et al. |
| 7,654,975 B2 | 2/2010 | Mantell |
| 7,704,223 B2 | 4/2010 | Mantell |
| 7,722,559 B2 | 5/2010 | Uesugi et al. |
| 7,806,850 B2 | 10/2010 | Williams, Jr. et al. |
| 7,918,816 B2 | 4/2011 | Ott et al. |

(56) References Cited

U.S. PATENT DOCUMENTS

| | | |
|---|---|---|
| 7,931,588 B2 | 4/2011 | Sarvazyan et al. |
| 7,938,793 B2 | 5/2011 | Mantell |
| 7,981,072 B2 | 7/2011 | Uesugi et al. |
| 8,057,448 B2 | 11/2011 | Williams et al. |
| 8,157,763 B2 | 4/2012 | Williams, Jr. et al. |
| 8,414,550 B2 | 4/2013 | Roberts et al. |
| 2001/0037063 A1 | 11/2001 | Albert et al. |
| 2001/0044576 A1 | 11/2001 | Vining |
| 2002/0045153 A1 | 4/2002 | Kaufman et al. |
| 2002/0161304 A1 | 10/2002 | Eide |
| 2002/0169415 A1 | 11/2002 | Staats et al. |
| 2002/0193687 A1 | 12/2002 | Vining et al. |
| 2003/0093503 A1 | 5/2003 | Yamaki et al. |
| 2003/0145849 A1 | 8/2003 | Drinan et al. |
| 2003/0158499 A1 | 8/2003 | Smith et al. |
| 2004/0030367 A1 | 2/2004 | Yamaki et al. |
| 2004/0059393 A1 | 3/2004 | Policker et al. |
| 2004/0102731 A1 | 5/2004 | Blackhurst et al. |
| 2004/0138586 A1 | 7/2004 | Ganz et al. |
| 2004/0193045 A1 | 9/2004 | Scarborough et al. |
| 2004/0230157 A1* | 11/2004 | Perry ............... A61M 5/14566 604/99.02 |
| 2005/0038374 A1 | 2/2005 | Williams, Jr. et al. |
| 2005/0097191 A1 | 5/2005 | Yamaki et al. |
| 2005/0107766 A1 | 5/2005 | Ott et al. |
| 2005/0137529 A1 | 6/2005 | Mantell |
| 2005/0222491 A1 | 10/2005 | Noda et al. |
| 2005/0222534 A1 | 10/2005 | Uesugi et al. |
| 2005/0222535 A1 | 10/2005 | Uesugi et al. |
| 2005/0245803 A1 | 11/2005 | Glenn, Jr. et al. |
| 2006/0004322 A1* | 1/2006 | Uesugi ............... A61M 13/003 604/26 |
| 2006/0030751 A1 | 2/2006 | Uesugi et al. |
| 2006/0047184 A1 | 3/2006 | Banik et al. |
| 2006/0052661 A1 | 3/2006 | Gannot et al. |
| 2006/0055544 A1 | 3/2006 | Morguelan |
| 2006/0058617 A1 | 3/2006 | Sano et al. |
| 2006/0079758 A1 | 4/2006 | Susi |
| 2006/0089571 A1 | 4/2006 | Gertner |
| 2006/0100500 A1 | 5/2006 | Williams |
| 2006/0129087 A1 | 6/2006 | Uesugi et al. |
| 2006/0253098 A1 | 11/2006 | Garabet |
| 2006/0257008 A1 | 11/2006 | Nolle et al. |
| 2007/0106209 A1* | 5/2007 | Williams ............ A61M 13/003 604/67 |
| 2007/0112299 A1 | 5/2007 | Smit et al. |
| 2007/0163585 A1 | 7/2007 | Uesugi et al. |
| 2007/0179432 A1 | 8/2007 | Bar Or et al. |
| 2007/0244363 A1 | 10/2007 | Sano et al. |
| 2007/0244424 A1 | 10/2007 | Hameed et al. |
| 2007/0255165 A1 | 11/2007 | Uesugi et al. |
| 2007/0265492 A1 | 11/2007 | Sonnenschein et al. |
| 2007/0282219 A1 | 12/2007 | Holte |
| 2007/0293734 A1 | 12/2007 | Coste-Maniere et al. |
| 2008/0133602 A1 | 6/2008 | Tashiro et al. |
| 2009/0036749 A1 | 2/2009 | Freiburger et al. |
| 2009/0048506 A1 | 2/2009 | Fong-Ichimura et al. |
| 2009/0143644 A1 | 6/2009 | Stiller et al. |
| 2009/0203995 A1 | 8/2009 | Matonick |
| 2010/0022834 A1* | 1/2010 | Noda .................... A61B 1/015 600/118 |
| 2010/0106080 A1 | 4/2010 | Uesugi et al. |
| 2010/0114011 A1 | 5/2010 | Herrmann |
| 2010/0130917 A1 | 5/2010 | Sezeur et al. |
| 2010/0185139 A1 | 7/2010 | Stearns et al. |
| 2010/0228100 A1* | 9/2010 | Vining ................. A61B 5/036 600/300 |
| 2010/0268153 A1 | 10/2010 | Mantell |
| 2010/0268154 A1 | 10/2010 | Vining |
| 2011/0030678 A1 | 2/2011 | Power et al. |
| 2011/0034862 A1 | 2/2011 | Williams, Jr. et al. |
| 2011/0060272 A1 | 3/2011 | Iranitalab |
| 2011/0066078 A1 | 3/2011 | Sarvazyan et al. |
| 2011/0263939 A1 | 10/2011 | Kaye et al. |
| 2012/0016293 A1 | 1/2012 | Hayashi |
| 2012/0157770 A1 | 6/2012 | Williams et al. |
| 2013/0102882 A1 | 4/2013 | Williams |

FOREIGN PATENT DOCUMENTS

| | | |
|---|---|---|
| CN | 102334973 A | 2/2012 |
| DE | 42 19 859 A1 | 12/1993 |
| DE | 92 18 373 U1 | 1/1994 |
| EP | 0 569 241 A2 | 11/1993 |
| EP | 1 101 506 A2 | 5/2001 |
| FR | 2 673 524 A1 | 9/1992 |
| JP | 48-43279 | 12/1973 |
| JP | 2-17141 | 2/1990 |
| JP | 4-27943 | 3/1992 |
| JP | 4-92249 | 8/1992 |
| JP | 4-297219 | 10/1992 |
| JP | 4-133845 | 12/1992 |
| JP | H05154094 A | 6/1993 |
| JP | H05226193 | 9/1993 |
| JP | 5-344950 A | 12/1993 |
| JP | 07-265261 A | 10/1995 |
| JP | 9-038092 A | 2/1997 |
| JP | 2006-014961 A | 1/2006 |
| JP | 2007-075396 A | 3/2007 |
| JP | 2008-093489 A | 4/2008 |
| JP | 2009-512535 A | 3/2009 |
| JP | 2010-227484 A | 10/2010 |
| WO | WO 00/69511 | 11/2000 |
| WO | WO 2005/120329 A1 | 12/2005 |
| WO | WO 2006/002635 A1 | 1/2006 |
| WO | WO 2007/050516 A2 | 5/2007 |
| WO | WO 2008/053485 A1 | 5/2008 |
| WO | WO 2009/052100 A2 | 4/2009 |
| WO | WO 2012/071399 A1 | 5/2012 |

OTHER PUBLICATIONS

International Search Report and Written Opinion for Application No. PCT/US2013/032005 dated Jun. 18, 2013.
Office Action for U.S. Appl. No. 13/402,455 dated Jan. 25, 2015.
Office Action for U.S. Appl. No. 13/711,802 dated Jan. 20, 2015.
Office Action for U.S. Appl. No. 14/459,365 dated Feb. 18, 2015.
Notice of Acceptance for Australian Application No. 2011331936 dated Feb. 10, 2015.
Office Action for Chinese Application No. 201180056406.6 dated Jan. 23, 2015.
Search Report for European Application No. EP 14 18 8116 dated Feb. 17, 2015.
Office Action for Japanese Application No. 2013-541016 dated Feb. 10, 2015.
Office Action for Korean Application No. 10-2013-7016190 dated Dec. 29, 2014.
International Search Report and Written Opinion of the Searching Authority for Application No. PCT/US05/46561; dated Sep. 13, 2007.
International Search Report and Written Opinion for Application No. PCT/US2006/041291 dated Sep. 13, 2007.
International Search Report for Application No. PCT/US02/37384 dated May 19, 2003.
International Preliminary Search Report for Application No. PCT/US2008/079826 dated Apr. 20, 2010.
International Search Report and Written Opinion for Application No. PCT/US2008/079826 dated Apr. 20, 2009.
International Preliminary Search Report for Application No. PCT/US2008/083115 dated May 18, 2010.
International Search Report and Written Opinion for Application No. PCT/US2008/038115 dated Apr. 24, 2009.
Examiner's First Report on Australian Patent Application No. 2006306361 dated Sep. 6, 2011.
Examination Report for Australian Patent Application No. 2011331936 dated Jun. 24, 2014.
Canadian Office Action for Application No. 2,642,135 dated Mar. 24, 2010.

(56) References Cited

OTHER PUBLICATIONS

Canadian Office Action for Application No. 2,642,135; dated Oct. 4, 2011.
Office Action for Chinese Application No. 200680043998.7 dated Jan. 29, 2010.
Translation of Second Notification of Office Action for Chinese Application No. 200680043998.7 dated Jul. 14, 2010 (5 sheets).
Office Action for Chinese Application No. 200680043998.7 dated Oct. 27, 2010.
Office Action for Chinese Application No. 201180056406.6 dated Jul. 3, 2014.
Supplementary European Search Report for Application No. EP 02 78 9809 dated May 28, 2009.
Office Action for Application No. EP 02 789 809.7 dated Oct. 22, 2009.
Communication from the Examining Division for EP Application 02 789 809.7, mailed Mar. 18, 2010; 8 pages.
Communication for European Application EP 02 789 809.7, dated Sep. 21, 2010.
EP Further Observations Under Art. 115 EPC for EP Application No. 02 789 809.7; mailed Oct. 15, 2010; 5 pages.
Intention to Grant for EP Application No. 02 789 809.7 dated Apr. 27, 2011.
Supplementary European Search Report for Application No. EP 08 84 0766 dated Apr. 10, 2014.
Office Action for European Application No. EP 08 84 0766.3 dated Apr. 29, 2014.
Extended European search report for EP Application No. 05 85 5170.6, mailed Jun. 4, 2010; 10 pages.
Office Action for European Application No. 05 855 170.6 dated Jan. 31, 2011.
Translation of EP1101506 Claims; EuropeanPatentOffice.pdf; Mehner, et al; Jul. 3, 2002; A61 M13/00; included with Notice of Allowance issued in U.S. Appl. No. 12/029,159, mailed Jun. 28, 2011.
Translation of EP1101506 Description; EuropeanPatentOffice.pdf; Mehner, et al; Jul. 3, 2002; A61 M13/00; included with Notice of Allowance issued in U.S. Appl. No. 12/029,159, mailed Jun. 28, 2011.
Espacenet—INPADOC patent family EP1101506.pdf; included with Notice of Allowance issued in U.S. Appl. No. 12/029,159, mailed Jun. 28, 2011.
Office Action for Japanese Application No. 2008-537841 dated Mar. 30, 2012.
Office Action for Japanese Application No. 2008-537841 dated Oct. 2, 2012.
Office Action for Japanese Application No. 2013-541016 dated Jun. 3, 2014.
Office Action for Korean Application No. 10-2008-7012245 dated Jan. 30, 2012.
Office Action for Korean Application No. 10-2008-7012245 dated Sep. 21, 2012.
Office Action for Korean Application No. 10-2013-7016190 dated Jun. 27, 2014.
Office Action for U.S. Appl. No. 11/257,229 dated Apr. 16, 2008.
Office Action for U.S. Appl. No. 11/257,229 dated Sep. 25, 2008.
Office Action for U.S. Appl. No. 11/257,229 dated Mar. 10, 2009.
Office Action for U.S. Appl. No. 11/257,229 dated Sep. 1, 2009.
Notice of Allowance for U.S. Appl. No. 11/257,229 dated Jun. 17, 2010.
Office Action for U.S. Appl. No. 11/315,049; dated Mar. 21, 2012.
Office Action for U.S. Appl. No. 12/742,358 dated Mar. 20, 2012.
Office Action for U.S. Appl. No. 12/742,358 dated Aug. 2, 2012.
Office Action for U.S. Appl. No. 12/845,475 dated Jul. 27, 2011.
Notice of Allowance for U.S. Appl. No. 12/845,475 dated Dec. 23, 2011.
Office Action for U.S. Appl. No. 13/267,434; dated Nov. 8, 2013.
Notice of Allowance for U.S. Appl. No. 13/267,434 dated Feb. 19, 2014.
Office Action for U.S. Appl. No. 14/459,365 dated Sep. 17, 2014.
"*Enema Container for X-ray in Large Bowel—Enemaunit*," Horri Pharm. Ind., Ltd., dated Oct. 1, 1977.
"*Enemaunit—disposable Implement for Intestinal Infusion Upon X-Ray Testing in Large Bowel*," Horii Pharm. Ind., Ltd., dated Jul. 1998.
"*E-Z-EM Balloon Inflators* Cat. No. 9529 [Ref 9529EU];" Merry X-Ray ; Product: 250422; retrieved on Nov. 14, 2013 from <http://orders.merryxray.com/webapp/wcs/stores/servlet/ProductDisplay?catalogId=11202&storeId=10051&productId=25341&langId=-l&parent_category_rn=20280&lvl0=19579&lvl1=19737&lvl2=&lvl3=>.
"*E-Z-EM Flexi-Cuff silicone elastomer retention cuff*;" Merry X-Ray—Product: 263980; retrieved on Nov. 14, 2013 <http://orders.merryxray.com/webapp/wcs/stores/servlet/ProductDisplay?catalogId=11202&storeId=10051&productId=25387&langId=-l&parent_category_rn=20280&lvl0-19579&lvl1=19737&lvl2=&lvl3=>.
"*E-Z-EM Flexi-Tip*;" Merry X-Ray—Product: 190005; retrieved on Nov. 14, 2013 from <http://orders.merryxray.com/webapp/wcs/stores/servlet/ProductDisplay?catalogId= 11202&storeId=10051&productId=25345&langId=-l&parent_category_rn=20280&lvl0= 19579&lvl1=19737&lvl2=&lvl3=>.
"*E-Z-EM hard bulb or E-Z-EM E-Z-Flat device*;" Merry X-Ray—Product: 292003; retrieved on Nov. 14, 2013 from <http://orders.merryxray.com/webapp/wcs/stores/servlet/ProductDisplay?catalogId=11202&storeId=10051&productId=25405&langId=-l&parent_category_rn=101313&lvl0=19579&lvl1=19737&lvl2=&lvl3=>.
PROTOCO₂L™, Automated Carbon Dioxide Insufflation System for Virtual Colonoscopy; E-Z-EM; Virtual Colonoscopy; retrieved on Dec. 9, 2005 from <http://www.ezem.com/virtual_colon/proto.htm>.
Office Action for U.S. Appl. No. 13/402,455 dated Aug. 13, 2015.
Office Action for Canadian Application No. 2,702,489 dated Jun. 1, 2015.
Office Action for Mexican ApplicationNo. MX/a/2013/005850 dated Jun. 25, 2015.
Office Action for U.S. Appl. No. 14/459,365 dated Jun. 24, 2015.
Office Action for Canadian Application No. 2,818,844 dated Aug. 19, 2014.
Notice of Allowance for corresponding Chinese Application No. 201180056406.6 dated Jul. 2, 2015.
Notice of Allowance for corresponding Canadian Application No. 2,818,844 dated Jul. 14, 2015.
Notice of Allowance for corresponding Korean Application No. 10-2013-7016190 dated Jul. 31, 2015.
Notice of Allowance for corresponding Japanese Application No. 2013-541016 dated Sep. 8, 2015.
Office Action for European Application No. 11 790 835.0 dated Oct. 14, 2015.
Office Action for U.S. Appl. No. 14/459,365 dated Nov. 3, 2015.
Office Action for U.S. Appl. No. 13/402,455 dated Jan. 20, 2016.

* cited by examiner

SYSTEM, DEVICE, AND METHOD FOR PROVIDING AND CONTROLLING THE SUPPLY OF A DISTENDING MEDIA FOR CT COLONOGRAPHY

CROSS-REFERENCE TO RELATED APPLICATIONS

This application claims priority from U.S. Provisional Application No. 61/417,017, filed Nov. 24, 2010 and U.S. Provisional Application No. 61/499,321, filed Jun. 21, 2011, which are hereby incorporated herein in their entirety by reference.

FIELD OF THE INVENTION

The present invention relates generally to gas insufflating devices often used in medical procedures to selectively distend one or more cavities defined within a subject's anatomy. More particularly, the present invention relates to a system and a method for providing and controlling the supply of insufflating gas to an insufflating device during a medical procedure.

BACKGROUND

Colorectal cancer, cancer of the large intestine and rectum, is second only to lung cancer in the amount of cancer deaths caused each year. Approximately 5% of all people will develop colorectal cancer within their lifetime. As is true with many other cancers, early detection of colon cancer or its precursors greatly increases chances of survival.

Precancerous polyps begin to form in the colon when cells in the lining of the intestine mutate and begin dividing rapidly. If left untreated, 8 to 12 percent of polyps will become cancerous tumors. Polyps sometimes bleed, and there may be some noticeable rectal bleeding that leads to early detection of precancerous growths. However, most of the time, this blood is invisible to the naked eye and is only detectable microscopically.

Gastrointestinal imaging can be used to accurately identify precancerous polyps and can thereby be used to prevent the development of colorectal cancer. The diagnostic performance of gastrointestinal imaging, including but not limited to computer tomography (CT) imaging and magnetic resonance imaging (MRI), may be facilitated by distending a desired body part prior to and during the diagnostic procedure. Ideally, distention is maintained throughout the procedure to obtain the most accurate image. Currently, it is known to distend the colon or other body parts of an individual prior to and during examination by direct connection of an insufflator to the proximal end of a rectal catheter or insertion tip that is inserted into the rectum of the individual. With this device, air or carbon dioxide ($CO_2$), for example, can be introduced into the colon. The sudden introduction of a sizeable amount of air or other gaseous media to an organ of the patient may cause the patient to experience discomfort or even pain.

Currently, the practice of using an electromechanical insufflator to comfortably control distension of the colon with carbon dioxide for radiographic imaging of the colon, typically referred to as CT colongraphy (virtual colonoscopy), is mostly utilized with computed tomography (CT) or magnetic resonance imaging (MRI) devices. Distending the colon with a gaseous media during such diagnostic procedures to open the colon's lumen provides a high to low contrast boundary defining its interior surface when exposed to X-rays when using a CT scanner. The radiologist can then view the resulting surface image in either 2-D or 3-D post scan to identify anatomic abnormalities, such as pre-cancerous growths, on the surface of the colon that could potentially represent a disease state in the colon. Currently, an operator of an electromechanical insufflator determines whether the organ of the patient to be scanned has been properly insufflated with the distending media by comparing the pressure and volume data from the insufflating device. In addition, an operator of the electromechanical insufflator may initiate a scout scan using the computed tomography or magnetic resonance imaging device to further evaluate whether the organ of the patient has been properly insufflated. Further, an operator of an electromechanical insufflator may be stationed in an adjacent viewing room to a CT suite where the patient and the insufflator is located. Thus, the operator may not be able to adjust or control the insufflator unless he is located in the CT suite with the patient and the insufflator.

Therefore, there exists a need for an insufflating system that is configured to simplify techniques for distending an organ for acquiring images as part of a medical imaging procedure. Moreover, there exists a need for an insufflating system that provides greater control over the delivery of the insufflating medium to safely deliver and distend an organ in a manner that is comfortable to the patient.

BRIEF SUMMARY OF THE INVENTION

Embodiments of the present invention improve the prior art by, among other things, providing an insufflating system adapted to be in fluid communication with a source of a distending media so as to deliver the distending media to an organ of a patient so as to acquire an image of the organ while distended with a computed tomography, magnetic resonance imaging, or other medical imaging device. According to one embodiment, the insufflating system includes an administration set, a controller, a user interface, and a valve assembly. The administration set may be configured to direct the distending media to the organ of the patient. The controller may be configured to detect at least one pressure and/or volume level or threshold within the organ of the patient. Further, the user interface may be configured to communicate with the controller and to signal an operator that proper insufflation or distension of the organ has been achieved for acquiring an image of the distended organ based on detecting at least one predetermined pressure and/or volume level or threshold. In addition, the valve assembly may be configured to be in communication with the controller and in fluid communication between the source of the distending media and the organ of the patient. According to another embodiment, the valve assembly may include an electro-pneumatic valve configured to adjust the flow rate of the distending media delivered to the organ of the patient in response to a signal delivered from the controller. The distending media may include, for example, carbon dioxide, anti-spasmodic gaseous media, relaxant gaseous media, ambient atmosphere, and/or any combination thereof.

The insufflating system may further comprise a data port and/or a wireless remote, both which are in communication with the controller. In one embodiment, the data port may be configured to transmit error or other reports to an external computing device. The remote may be configured to allow a user to operate the insufflating device from a remote location (e.g., remote from the insufflating system) without interacting with the user interface.

The insufflating system may further include a security assembly configured to ensure operability of, and allow for fluid communication between, the administration set and a distending device associated with the controller and the valve assembly. Further, the security assembly may be configured to allow operation of the dispensing device only upon determining that the administration set has not been previously used. In addition, the security assembly may include a specialized or proprietary connector associated with the dispensing device and/or the administration set that facilitates engagement between the administration set and the dispensing device. For example, the administration set may be required to have a particular connector that is only configured to engage a mating connector associated with the dispensing device.

The administration set may also include a filter device in fluid communication with the valve assembly and the insertion tip may be configured to prevent a pathogen from passing from the insertion tip to the valve assembly. The filter device may be a biological or a hydrophobic filter. In addition, the administration set may also include a collection assembly disposed between the insertion tip and the filter device and in fluid communication therewith. The collection assembly may be configured to collect any pathogens, liquids, or other undesired waste from the organ of the patient so as to prevent contamination of the source of distending media.

The insufflating system may also include a user interface, according to one embodiment of the invention, configured to receive user input, which may include a desired pressure and/or volume level, such as a flow pause volume level, a desired flow extension volume level, a desired first target pressure level and/or a desired final target pressure level within the organ of the patient. Further, the user interface may be configured to display the volume of distending media delivered to the patient, the volume of distending media remaining in the source of distending media, the current pressure within the organ of the patient, the distending media flow status, the vent status, the pressure status of the distending media source, and/or a ready-to-scan indicator.

In one embodiment, the insufflating system may be configured to pause the flow of distending media when the volume of distending media dispensed equals the predetermined flow pause volume level. The insufflating system may also be configured to dispense an additional volume of distending media after the flow has been paused equal to the predetermined flow extension volume as selected by the user.

In an additional embodiment, the insufflating system may also include a relief valve assembly in communication with the controller and in fluid communication between the source of the distending media and the administration set. The controller is configured to actuate the relief valve assembly if a pressure within the administration set or the organ of the patient exceeds a pressure level for a predetermined period of time.

In another embodiment, the insufflating system may be configured to pause and/or regulate the flow of distending media when the pressure of the distending media dispensed equals a first target pressure level. The insufflating system may also be configured to display an indicator to the operator for checking the patient. In addition, the insufflating system may also be configured to resume the flow of distending media until a final target pressure level is achieved and may be further configured to regulate the flow of distending media to maintain the final target pressure within the lumens and/or an organ of the patient. In addition, according to another embodiment, the insufflating system may be configured to detect a pressure level of the distending media within the organ of the patient and may be configured to provide an indication that proper distension has been achieved for acquiring an image of the organ based on the pressure level being within a predetermined pressure range for a predetermined period of time.

Associated methods for delivering distending media to an organ of a patient with a dispensing device for acquiring an image of the organ while distended are also provided. According to one embodiment, a method for delivering distending media to an organ of a patient with a dispensing device for acquiring an image of the organ while distend is provided. The method may comprise delivering the distending media to the organ of the patient and detecting a pressure level of the distending media within the organ of the patient. Further, the method may also include providing an indication that proper distension has been achieved for acquiring an image of the organ of the patient based at least on the pressure level being within a predetermined pressure range for a predetermined period of time. According to another embodiment, the method may include detecting at least one predetermined volume level of the distending media delivered to the organ. In one embodiment of the present invention, the method may further comprise providing an indication that proper distension has been achieved for acquiring an image of the organ of the patient based on the pressure level being within the predetermined pressure range for the predetermined period of time and the at least one detected volume level.

According to another embodiment of the present invention, a method for delivering distending media to an organ of a patient with a dispensing device for acquiring an image of the organ while distension is provided. The method may include delivering the distending media to the organ of the patient. In addition, the method may comprise pausing delivery of the distending media in response to detecting at least one predetermined pressure level of the distending media delivered to the organ. According to one embodiment, the method may further comprise resuming delivery of the distending media in response to a selection. The method may further include ceasing delivery of the distending media in response to detecting a second predetermined pressure level.

Additionally, embodiments of the present invention may combine some or all of the embodiments discussed herein. For instance, in one embodiment, the insufflating system may include any combination of an administration set, a controller, a user interface, a valve assembly, a data port, and a wireless remote.

BRIEF DESCRIPTION OF THE DRAWINGS

Reference will now be made to the accompanying drawings, which are not necessarily drawn to scale. The drawings are for illustrative purposes only, and are not intended to limit the scope of the present invention.

DETAILED DESCRIPTION

The present invention will be described with reference to the accompanying drawings, where applicable. It is understood that the present invention may be embodied in many different forms and should not be construed as limited to the embodiments set forth herein; rather, these embodiments are provided for illustrative purposes only. Like numbers refer to like numbers throughout.

While the embodiments of the system and method for delivering distending media are described below in the context of providing insufflating media comprising carbon dioxide for CT colonography (virtual colonoscopy), it should be understood that the embodiments of the present invention may also be utilized to provide a precisely controllable supply of distending media of various types (including various gas mixtures and media containing relaxants and/or non-spasmodic agents) to a variety of different endoscopic and/or laparoscopic instruments requiring a supply of distending media. Moreover, although the discussion below relates to CT colonography by distending the colon, it is understood that embodiments of the present invention may be utilized with any organ capable of being distended with a distending media for obtaining an image thereof. In addition, the distended organ may be imaged using various imaging techniques, such as CT and MRI.

Figure 1:
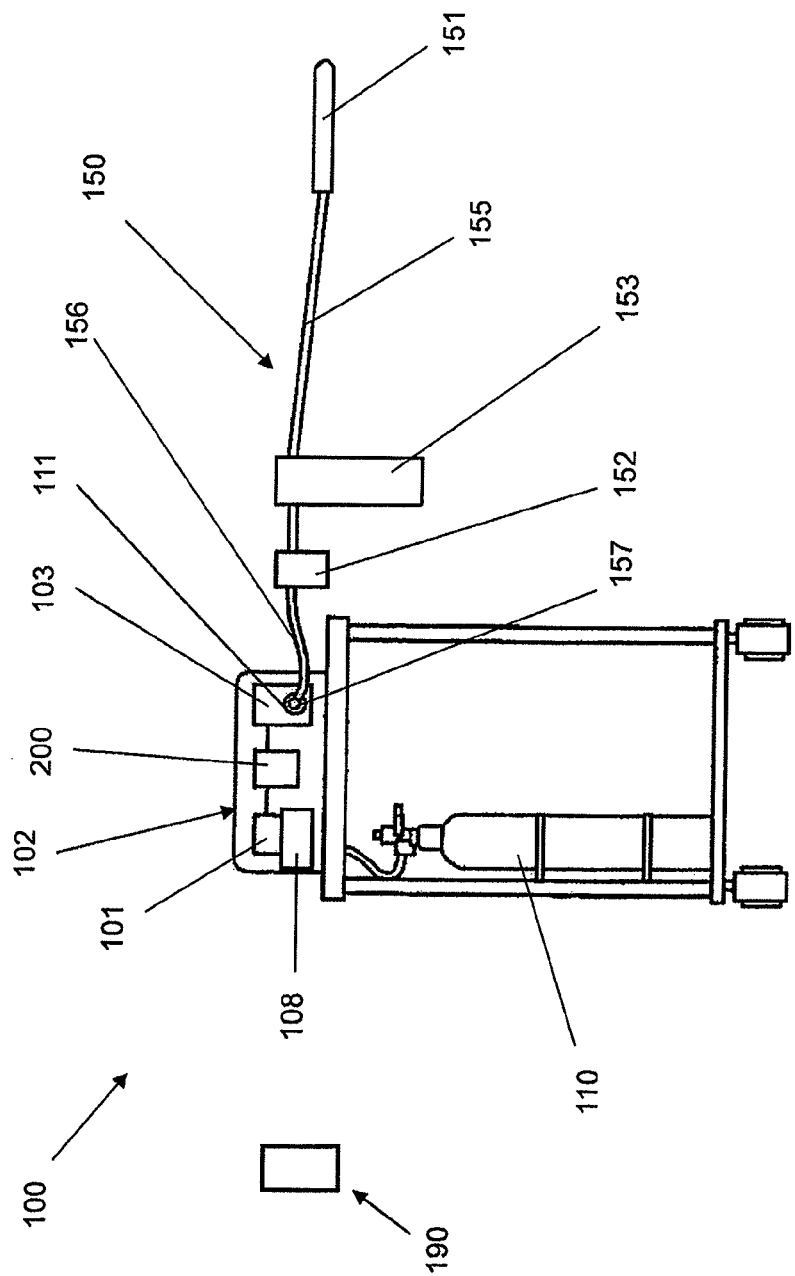
FIG. 1 illustrates an insufflating system for distending an organ in accordance with one embodiment of the present invention.

FIG. 1 shows an insufflating system 100, according to one embodiment of the present invention. The insufflating system 100 generally includes an insufflating device 102 or insufflator in fluid communication with a source 110 of a distending media (such as a bottle of insufflating gas) and an administration set 150 so as to be capable of delivering the distending media to a patient according to one embodiment of the present invention. According to some embodiments, the insufflating device 102 comprises a controller 101 for detecting a pressure level of the distending media delivered to the patient. The insufflating device 102 may also comprise a valve assembly 103 in communication with the controller 101 for delivering the distending media to the patient at a desired flow rate. One advantageous aspect of the present invention includes providing an indication to the operator of the insufflating system 100 when the patient has been properly distended for acquiring an image. As shown in FIG. 1, the insufflating system 100 of the present invention may be operably engaged with a remote control unit 190 configured to operate the insufflating system. Further, the insufflating system 100 may further comprise a user interface 200, the user interface being in communication with the controller 101 and the valve assembly 103 and being further configured to interface therewith.

Some embodiments of the present invention may comprise, as generally shown in FIG. 1, an insufflating system 100 including an insufflating device 102, such as an electropneumatic insufflator, connected to an administration set 150. The administration set 150 may comprise a security assembly 157, a filter device 152, an insertion tip 151, a collection assembly 153, and a plurality of connecting lumens 155, 156. Connection between the insufflating device 102 and the insertion tip 151 of the administration set 150 may be accomplished via the plurality of lumens 155, 156 disposed between an outlet 111 of the insufflating system 100 and the insertion tip 151. According to various embodiments of the present invention, the lumens 155, 156 of the administration set 150 may comprise disposable medical-grade and/or biocompatible tubing that may be replaced and/or discarded after each use. Thus, the insufflating device 102 of the present invention would otherwise be isolated from pathogens that may be introduced into the valve assembly 103 or the source of distending media 110 during the course of a CT colonography procedure.

Furthermore, some embodiments of the insufflating system 100 of the present invention may further comprise a filter device 152 in fluid communication between an output of the valve assembly 103 of the insufflating system 100 and the insertion tip 151 of the administration set 150. In other embodiments, the filter device may be disposed between the source of the distending media and the output of the valve assembly. Further, other embodiments may include an insufflating system comprising a filter device integrated with an insufflating device and/or integrated with portions of a tubing set of the insufflating device. In some embodiments, as shown in FIG. 1, the filter device 152 may be in operably engaged in fluid communication between an output of the valve assembly 103 of the insufflating system 100 and a collection assembly 153 so as to prevent passage of a pathogen from the collection assembly 153 to the valve assembly 103 of the insufflating system 100 of the present invention. For example, should waste or other liquid products exceed the capacity of the collection assembly, the filter device 152 may prevent the passage of a pathogen from the overflow of the waste or other liquid products to the valve assembly 103. According to various system embodiments of the present invention, the filter device 152 may include, but is not limited to: a biological filter, a hydrophobic filter, and combinations thereof.

According to further embodiments of the present invention, the insufflating device 102 and/or the administration set 150 may further comprise a security assembly 157 associated therewith. The security assembly 157 may be configured to allow for fluid communication between an output of the valve assembly 103 and the administration set 150 and may be further configured to communicate with the controller. Specifically, the security assembly 157 may communicate with the controller 101 prior to the commencing flow of distending media from the source 110 to the administration set 150. In one embodiment, the security assembly 157 may signal the controller to prohibit the flow of distending media to the administration set 150 if the security assembly detects the administration set has been used before, thus further preventing the possibility of a pathogen entering the valve assembly 103. In another embodiment, the controller may automatically prohibit flow of distending media if the security assembly 157 is not present to signal the controller to commence flow. Thus, the insufflating device 102, according to one embodiment, may not function unless the insufflating device 102 or the administration set 150 comprises the appropriate security assembly 157. In some embodiments, the security assembly 157 may comprise a radio-frequency identification (RFID) device associated with the insufflating device 102 or the administration set 150. In other embodiments, the security assembly 157 may comprise electrical circuitry containing a unique identifier. For example, an electrical chip may include a unique identifier associated with the administration set that can be read by the dispensing device to verify that an administration set has not been previously used. Further, the security assembly 157 may comprise chip technology, a USB device, or other electrical connector circuitry configured to engage the dispensing device and communicate with the controller such that the controller permits flow of distending media only when an appropriate identifier is verified or otherwise identified. In addition, the security assembly 157 may include a connection at the outlet 111 that is only capable of cooperatively engaging with a particular administration set 150. For instance, the tubing of the administration set 150 may include a connector that is only capable of engaging a mating connector on the outlet 111, such as via a quick-disconnect connection. Thus, a security assembly 157 may be employed to ensure operability of the insufflating device 102, including the controller 101 and the valve assembly 103, based on a determination whether the insufflating device and the administration set 150 are compatible with one another and/or a determination whether the administration set has been used previously.

Figure 5:
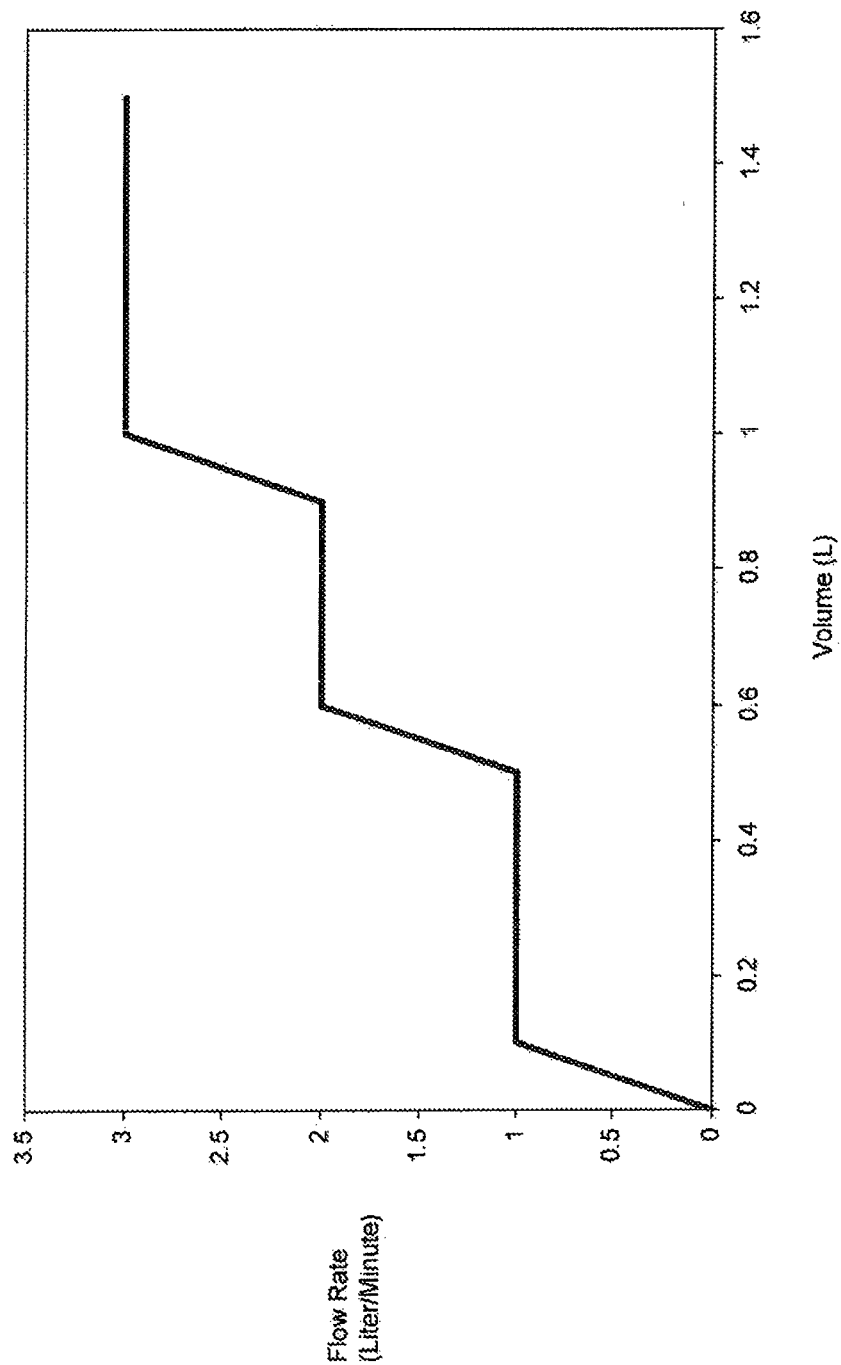
FIG. 5 illustrates a tiered flow rate of distending media according to one embodiment of the present invention.

As one skilled in the art will appreciate, conventional colonoscopy insufflators may require a nominal flow rate in order to properly insufflate the colon in a subject. For example, the flow rate may include providing distending media at a rate of at least about 1 liter per minute and at a maximum delivery pressure of about 35 mm Hg. These exemplary performance specifications are independent of the type of insufflating media (e.g., $CO_2$ or room air) and method of delivery (e.g., an air pump or insufflating system as provided by the various embodiments of the present invention). According to some insufflating system 100 embodiments, the valve assembly 103 may comprise an electro-pneumatic valve assembly or other electromechanical mechanism for controlling the flow rate of a distending media that may be delivered from a source 110 (such as a bottle of compressed carbon dioxide or other gas or other gas mixture) via the insufflating device 102 in response to the pressure levels detected by the controller 101 (and/or a pressure transducer that may be provided therein) and/or in response to the volume of distending media dispensed to the patient. According to the various embodiments of the present invention, the insufflating flow rate may be between about 1 and 5 liters per minute. In one embodiment, the insufflating flow rates may be initially set prior to the commencement of the insufflation based on the volume of dispensing media to be delivered. Specifically, in one embodiment, the insufflating flow rate may be about 1 liter per minute when the insufflating device 102 has dispensed about 0 to 0.5 liters of distending media, may be about 2 liters per minute when the insufflating device 102 has dispensed about 0.6 to 1 liters of distending media, and may be about 3 liters per minute when the insufflating device 102 has dispensed more than about 1 liter of distending media, as shown in FIG. 5.

Figure 6:
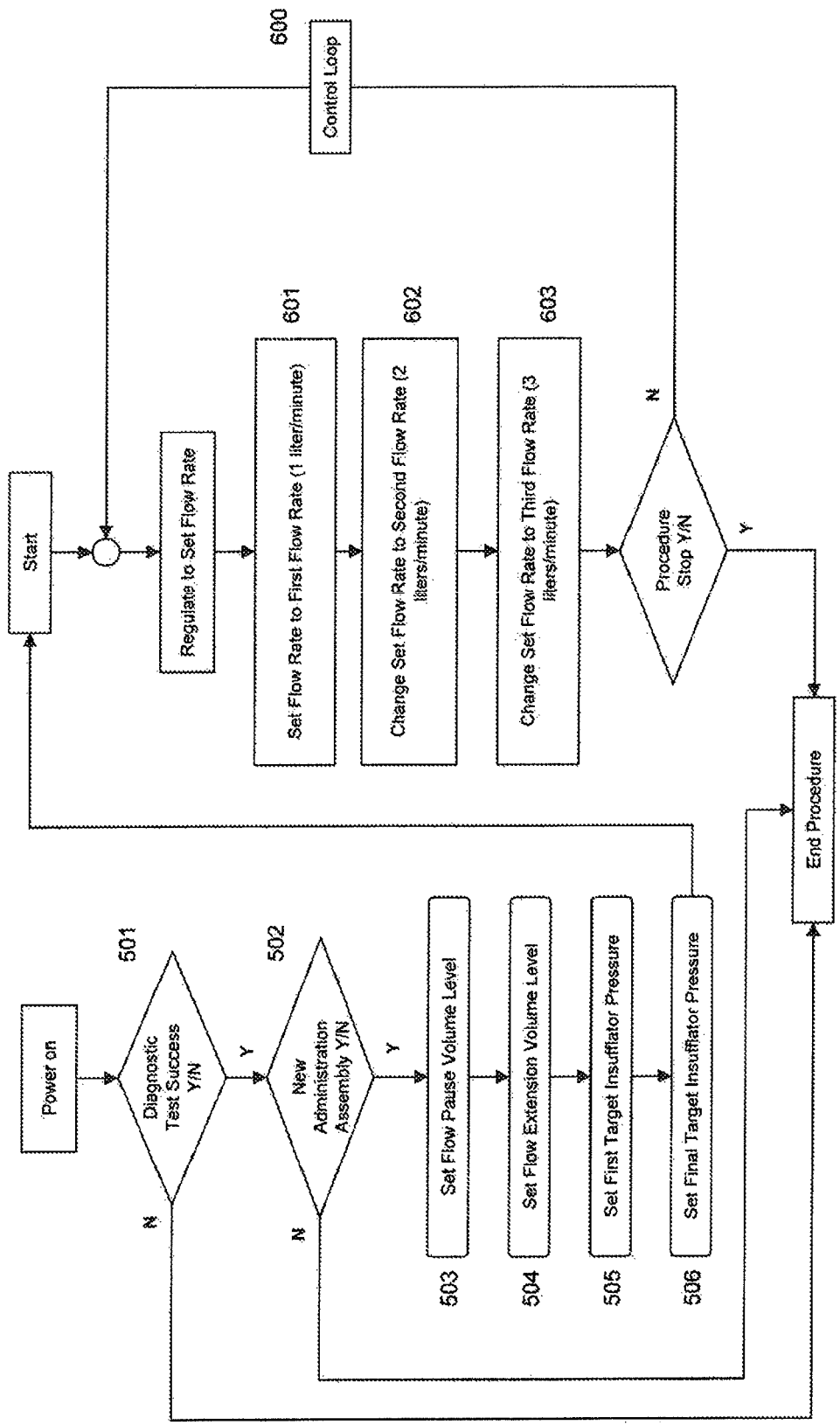
FIG. 6 illustrates a method of providing distending media to an organ of a patient according to one embodiment of the present invention.

FIG. 6 illustrates a flow chart of a method of supplying distending media to an organ of the patient. The insufflating system begins supplying distending media by initially performing a diagnostic test 501 to determine whether the system is functioning properly. After successful completion of the diagnostic test, the controller and the security assembly 157 determine whether the administration set has been previously used and/or whether the proper administration set is connected to the insufflating system 502. The operator may then input a first flow pause volume level 503, a second flow extension volume level 504, a desired first target insufflation pressure level 505 and a desired final target insufflation pressure level 506. In one embodiment, the final pressure level 506 is greater than the first pressure level 505. Once the operator has inputted the desired values for the various volume and/or pressure thresholds, the operator may commence the flow of distending media to an organ of the patient. The insufflating system will dispense distending media to an organ of the patient and regulate the flow of distending media via a control loop 600. The controller may be configured to detect the volume of distending media delivered. In addition, another embodiment of the present invention may be further configured to allow an operator to selectively provide an on-demand flow of the insufflating media at a predetermined flow rate. In particular, the flow rate may be adjusted during the procedure based on the volume delivered, with a first flow rate 601, a second flow rate 602, and a third flow rate 603 dependent upon the volume of distending media provided to the organ of the patient.

According to various insufflating system 100 embodiments of the present invention, the controller 101 may comprise a pressure transducer or sensor for detecting a pressure of the distending media delivered to the patient. In other words, the controller 101 can detect the pressure within the organ being distended. Some embodiments of the insufflating system 100 may comprise an in-line outlet pressure transducer (as part of the controller 101) that may measure pressure levels at the insertion tip 151 of the administration set 150. In some embodiments, the controller 101 may be capable of detecting a pressure within a lumen 155, 156 of the administration set 150. In other embodiments, the controller 101 may be capable of detecting pressure with an internal lumen internal to the insufflating device 102. The outlet pressure transducer may thus be capable of detecting the pressure within the insufflating device, the administration set, and/or the organ of the patient as an operator conducts a CT colonography procedure. During the course of the procedure the controller 101 may monitor the output of the pressure transducer. In some system embodiments of the present invention, the controller 101 may further comprise a memory device 108 in communication therewith for storing, for example, a pressure level or threshold and/or a volume level or threshold.

Figure 9:
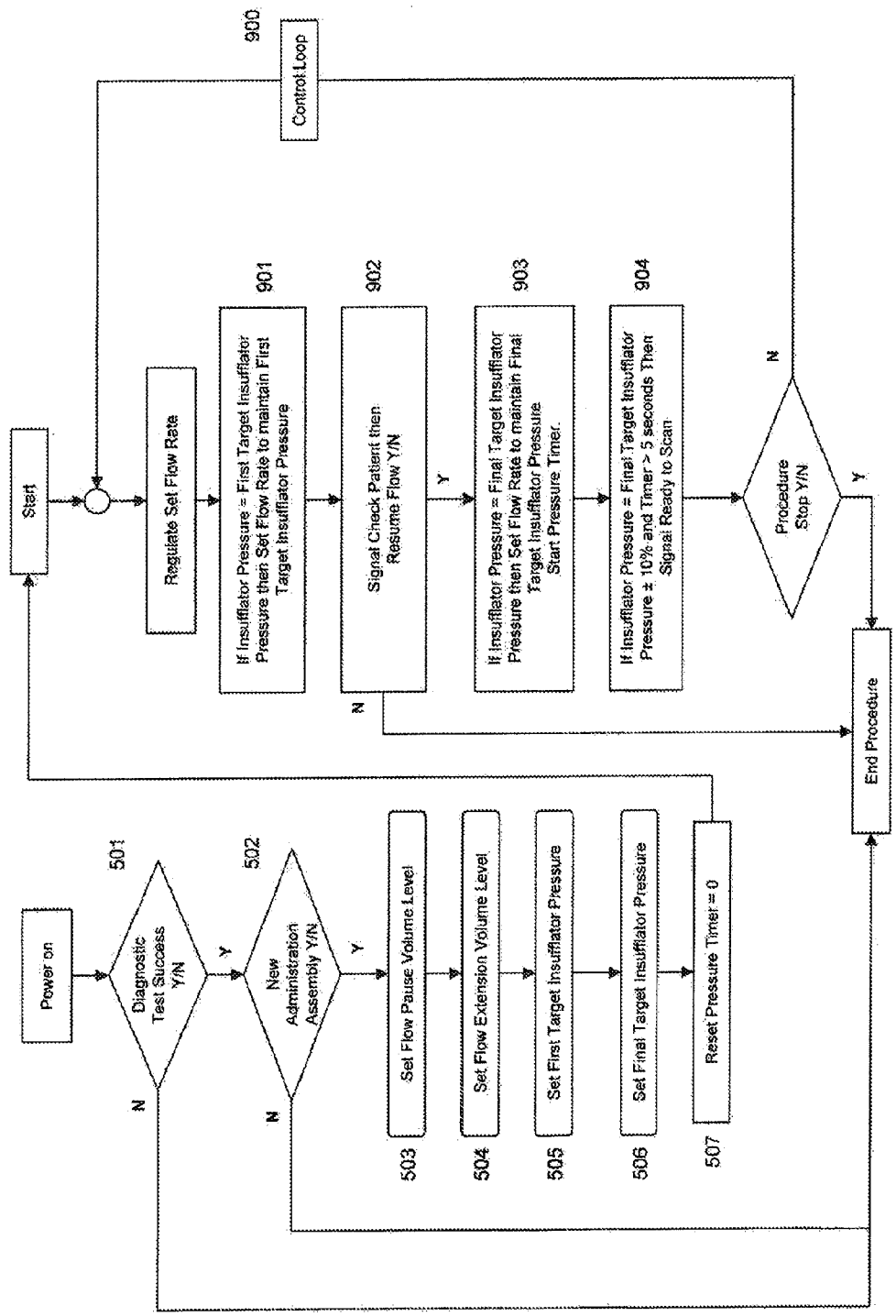
FIG. 9 illustrates a method of providing distending media to an organ of a patient with an insufflating device configured to regulate the flow of distending media according to one embodiment of the present invention.

FIG. 9 illustrates a flow chart of a method of supplying distending media to an organ of a patient. According to one embodiment, the insufflating system initially performs a diagnostic test 501 to determine whether the system is functioning properly. After successful completion of the diagnostic test, the controller and the security assembly 157 determine whether the administration set has been previously used and/or whether the proper administration set is connected to the insufflating system 502. The operator may then input a first flow pause volume level 503, a second flow extension volume level 504, a desired first target insufflation pressure level 505 and a desired final target insufflation pressure level 506. Once the operator has provided the desired levels, the controller may reset a timer for measuring a period of time when the pressure within the insufflating device, the administration set, and/or the organ of the patient has reached and/or exceeded at least one pressure level 507.

Specifically, FIG. 9 illustrates a flow chart of a method of delivery distending media to an organ of the patient that includes a controller configured to regulate the flow of distending media to the organ of the patient based in part on detecting the pressure within the organ being distended. The controller may be configured to pause and/or regulate the flow of insufflating media if the controller detects a pressure that is substantially equal to a first target insufflator pressure level 901. Further, the controller may be configured to provide a signal and/or communicate with the user interface for providing a status indication to the operator to check the patient 902. The operator, after checking the patient, may then resume the flow of distending media such as by touching a "Resume Flow" button displayed on the user interface. The controller may be configured to resume the flow of distending media to the organ of the patient and be further configured to pause and/or regulate the flow of insufflating media if the controller detects a pressure that is substantially equal to a desired final target insufflation pressure level 903. Once the controller detects a pressure that is substantially equal to the desired final target insufflation pressure level, the controller may be further configured to initiate a timer to measure whether the pressure remains substantially equal to the desired final target insufflation pressure level for a specified time period or is within a predetermined pressure range for a predetermined period of time. If a predetermined volume has been delivered and the pressure within one of the lumens of the insufflating system and/or an organ of the patient remains within the pressure range for a predetermined period of time, the controller may be configured to provide a signal and/or communicate with the user interface to indicate that the patient is ready for scanning, such as by providing a "ready to scan" indicator to the operator 904. In one embodiment, the user may be ready to scan when the volume delivered is about 2 to 5 liters and pressure is within about 10 mm Hg from the final target pressure level for a predetermined period of time about 5 seconds. Thus, a predetermined pressure range could be set based on the final target pressure level. For example, if the final target pressure level is 20 mm Hg, the predetermined pressure range could be about 18-22 mm Hg.

According to one embodiment, the controller may be configured to regulate the flow of distending media such that the pressure within the organ of the patient is no greater or less than 10 percent of the final target insufflation pressure level if the final target insufflation pressure level is greater than 10 mm Hg after the controller first detects the pressure within the organ of the patient is substantially equal to the final target insufflation pressure. In another embodiment, the controller may be configured to regulate the flow of distending media such that the pressure within the organ of the patient is no greater or less than 1 mm Hg of the final target insufflation pressure level if the final target insufflation pressure level is less than 10 mm Hg after the controller first detects the pressure within the organ of the patient is substantially equal to the final target insufflation pressure. Further still, in one embodiment, an operator may selectively deactivate the first target insufflation pressure and the controller may be configured to provide distending media until a pressure substantially equal to the final target insufflation pressure is detected within the organ of a patient. In another embodiment, the final target pressure may be displayed on the user interface throughout the procedure. According to another embodiment, the operator may selectively modify the final target pressure by interacting with the user interface displaying the final target insufflation pressure during the operation.

Figure 8:
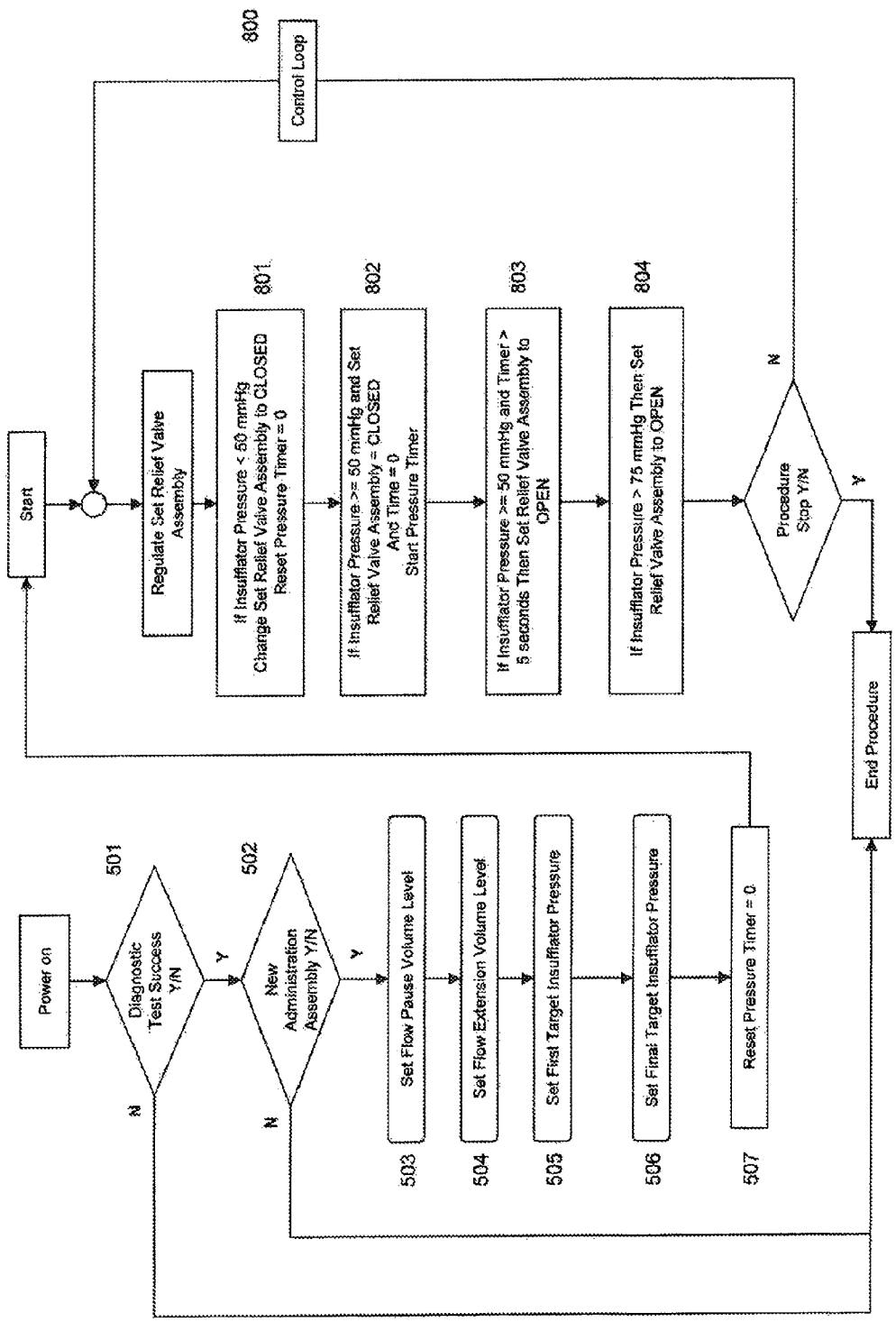
FIG. 8 illustrates a method of providing distending media to an organ of a patient with an insufflating device configured to vent the distending media from the organ of the patient according to one embodiment of the present invention.

Further, one embodiment of the present invention may also include a relief valve assembly (not shown) in communication with the controller 101 that is configured to be actuated once a predetermined pressure level or threshold has been reached. FIG. 8 illustrates a flow chart of a method of delivering distending media to an organ of the patient that includes a relief valve assembly configured to vent distending media if the controller detects a pressure that exceeds a predetermined first pressure level for a predetermined period of time 803. The relief valve assembly is further configured to vent distending media if the controller detects a pressure that exceeds a second pressure level 804. The controller may be configured to measure the pressure within the lumens of the insufflating system and/or an organ of the patient. In one embodiment, the controller may be configured to close the relief valve assembly if the pressure within the lumens of the insufflating system and/or an organ of the patient does not exceed a first pressure threshold 801. If the pressure within one of the lumens of the insufflating system and/or an organ of the patient exceeds a first pressure threshold, the controller may be configured to initiate a timer to measure whether the pressure exceeds the first pressure threshold for a specific predetermined period of time 802. In one embodiment, the controller may be configured to actuate the relief valve assembly and vent the distending media to the outside environment if a pressure exceeds a specific pressure level for a specific predetermined period of time 803. For example, the controller may actuate the relief valve assembly and vent the distending media if the controller detects a pressure that exceeds about 50 mmHg for a period of five seconds 803. In addition, the controller may be further configured to actuate the relief valve assembly if the controller detects a pressure that exceeds a second specified predetermined pressure 804. In one embodiment, the second specified pressure may be at least about 75 mmHg. Further, the relief valve assembly may further comprise a pressure relief valve controlled by a software program and a mechanical pressure relief valve. The relief valve assembly may be further configured so that the pressure relief valve controlled by a software program will actuate and vent distending media to the outside environment if the controller detects a pressure that exceeds a specified pressure level for a specified period of time. The relief valve assembly may also be configured such that the mechanical pressure relief valve may be actuated and automatically vent distending media to the outside environment when the pressure within the insufflating system 100 exceeds a second specified pressure level.

As shown generally in FIG. 1, various embodiments of the insufflating system 100 illustrate that the insufflating device 102 may be in fluid communication between an administration set (including, for example, a filter 152, a collection assembly 153, and a insertion tip 151) and a source 110 of distending media, such as a bottle of compressed insufflating media. According to various embodiments of the present invention, the distending media may include, but is not limited to: carbon dioxide; anti-spasmodic gaseous media; relaxant gaseous media; and combinations of such media that may serve as distending media in an endoscopic procedure. While embodiments of the present invention are particularly useful for conserving bottles distending media (such as carbon dioxide), the insufflating system 100 embodiments of the present invention may also be used to deliver distending media from a variety of sources 110, including for example, bottles of compressed air (including nitrogen components).

Figure 2:
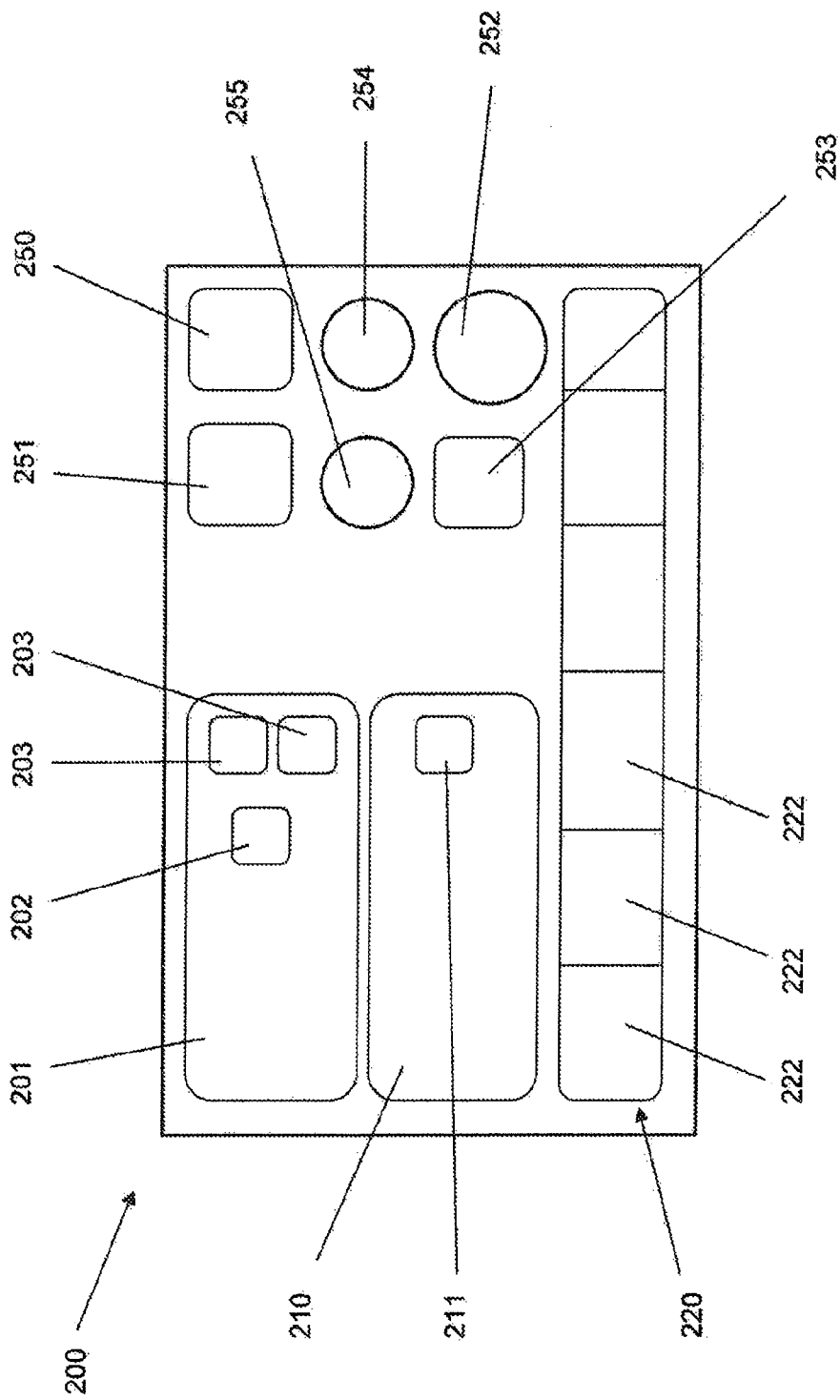
FIG. 2 illustrates a user interface of an insufflating system according to one embodiment of the present invention.

Some embodiments of the insufflating system 100 of the present invention may further comprise a user interface 200 (see FIG. 2) configured to display data to an operator of the system. The user interface 200 may be further configured for receiving a user input, such as pressure and/or volume thresholds, such that the insufflating system 100 may adequately respond to the amount of distending media delivered to the patient. As shown in FIG. 2, the user interface 200 may comprise a front touch screen display panel of the insufflating device 100. The user interface 200 may be configured to illustrate a variety of informational displays to display the status of the insufflating system 100 (and/or the status of the distending media supply 110 or components of the administration set) during operation of the insufflating device 102. In one embodiment, the user interface 200 allows the user to select a particular source 110 of distending media. For example, the user may select a tank or wall source as the source 110 of distending media. In addition, the user interface 200 may allow the user the ability to switch between different types of sources 110 of distending media.

For example, as shown in FIG. 2, the user interface 200 may comprise a pressure display 201 configured to display the current pressure. The pressure display 201 may further comprise a final target pressure display 202 and pressure adjustment buttons 203. The operator may, before or during operation of the insufflating device 100, select a specified final target pressure level by pressing the pressure adjustment buttons 203. In one embodiment, the selected pressure display 202 will display the pressure and will increase the selected pressure upon the operator engaging the increasing pressure adjustment button, and will decrease the selected pressure upon the operator pressing the decreasing pressure adjustment button. In addition, the user interface 200 may comprise a volume display 210 configured to display the amount of distending media that has been delivered to the administration set 150. The volume display 210 further comprises a volume reset button 211 configured to reset the indicated amount of distending media that has been delivered to the administration set to zero (e.g., to reset the display when a new procedure is initiated).

The user interface 200 further comprises a status bar 220, the status bar comprising status portions 222 and configured to display a plurality of information regarding the status of the insufflating system such as the flow status, the distending media source status, the distending status of the patient, a check patient status alert and/or the vent status. For example, the status bar will display a gas cylinder icon within one of the status portions to indicate the insufflating device 102 is properly connected to the source 110 of the distending media, and that the pressure of the source of distending media is at a proper level. The status bar may also display the flow status within one of the status portions to indicate the source of distending media is flowing through the insufflating system 100 and the administration set 150 to the patient. Further, the status bar may display the distending status of the patient within a status portion when the patient has been properly distended. In addition, the status bar 220 may further be configured to display a vent status within one of the status portions to indicate the insufflating system 100 is venting the distending media to the environment after a CT colonography procedure has finished or has been selectively stopped by the user.

Figure 11:
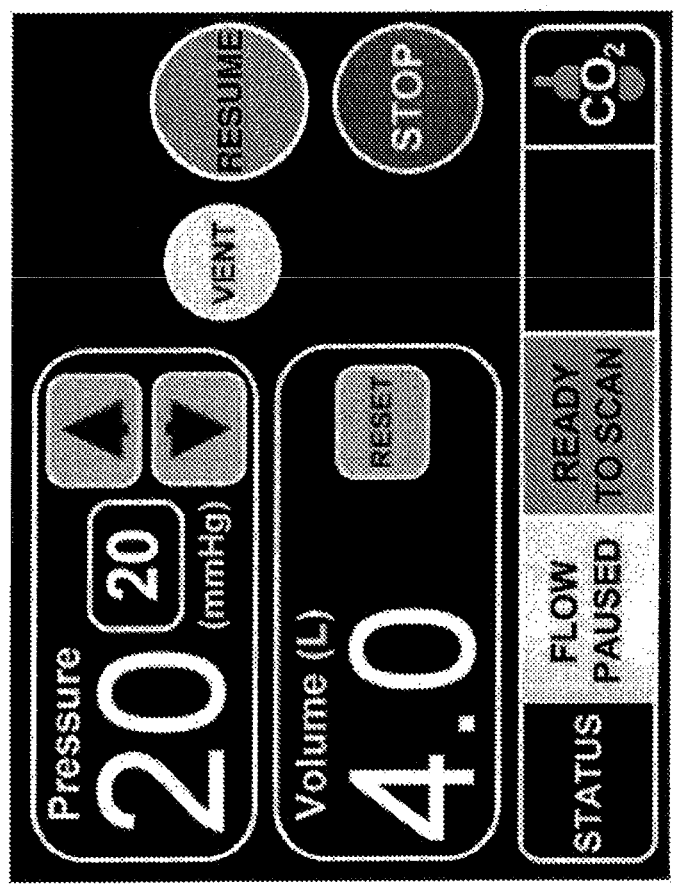
FIG. 11 illustrates a user interface of an insufflating system according to one embodiment of the present invention.

One advantage of the embodiment of the present invention includes notifying the operator with a visual indicator that the patient is properly distended, as shown as a "ready to scan" indicator in FIG. 11, which allows the insufflating device to quickly inform the operator to initiate a scan from a computed tomography (CT) device or other imaging device in order to perform a CT colonography or other procedure. The controller may be configured to calculate whether a patient is properly distended based on a pressure of distending media within the organ of the patient and/or a volume of distended media delivered to the organ of the patient. In contrast to the "ready-to-scan" feature of the present invention, operators typically use data visible on the face of the insufflating devices to make a determination as to when the correct time to scan is. Thus, by providing a distending status indicator according to embodiments of the present invention, the operator is provided with a clear and accurate indicator which may streamline the CT colonography procedure. In one embodiment of the present invention, the controller may be configured to signal an operator that a patient is ready to be scanned when the pressure within an organ of the patient reaches an equilibrium point for a predetermined period of time. Due to the fluctuations in pressure that may result depending on the patient or patient's activity during the insufflation procedure, the equilibrium point may be, for instance, a predetermined pressure level that does not signify a pressure that has plateaued or achieves steady state but, rather, is a particular value that indicates that the patient is ready to be scanned. Such an equilibrium point may be selectively determined by the operator as a pressure point or predetermined final target pressure level that can be used for a number of different patients. Further, in another embodiment, the equilibrium point may be established on a patient-by-patient basis and/or by the personal preference of an individual physician. The patient may also be deemed ready to be scanned based on a predetermined volume of distending media provided to the patient. Thus, the patient is ready to be scanned when the predetermined pressure level is reached for a predetermined period of time and a predetermined volume of distending medium has been delivered. In another embodiment, the equilibrium point may be selectively determined by an operator as a predetermined pressure level when the volume of distending media dispensed is greater than or equal to a predetermined volume level, such as, for example, about 3 liters.

Another advantage of the embodiment of the present invention includes providing the operator with a wireless remote 190, as shown in FIG. 1, that is configured to remotely operate the insufflating system 100. Typically, operators must control insufflating devices by manipulating user interfaces and/or controls located directly on the insufflating device. Moreover, insufflating devices are used in conjunction with a computed tomography (CT) imaging device and/or a magnetic resonance imaging (MRI) device, which may require the insufflating device to be located in a suite that houses the medical imaging device. Thus, the wireless remote 190 provides the operator with a device to control the insufflating system while being removed from the medical imaging device suite, thus limiting the operator from continuous exposure to radiation produced by the medical imaging device.

The user interface 200 may further comprise a plurality of buttons (e.g., pressure adjustment buttons 203, Start/Stop button 252, etc.), as shown in FIG. 2, that are configured to interact with the user and control the insufflating device 100. Specifically, the user interface 200 may comprise a power on/off button 250, a menu button 251, a start/stop control button 252, an alarm alert/mute button 253, a flow extend button 254, and a vent button 255. In addition to a power on/off rocker switch (not shown), a power on/off button 250 may be configured for shutting off electrical power to the controller 101, valve assembly 103 and/or other components of the insufflating system 100 when the system is not in use. The menu button 251 may be configured to display the menu settings of the insufflating system 100 on the touch screen display of the user interface 200. In one embodiment, the operator may configure various menu settings, some of which may comprise displaying a particular language to the user interface, selecting the source from where the distending media will be dispensed (e.g., a continuous wall outlet and/or a gas cylinder), selecting a default volume level, selecting a default pressure setting for distending a cavity of an organ of the patient, and resetting the various menu settings to a factory authorized default setting. The start/stop control button 252 may be configured for selectively beginning and/or ceasing the flow of distending media via the insufflating system 100.

Figure 12:
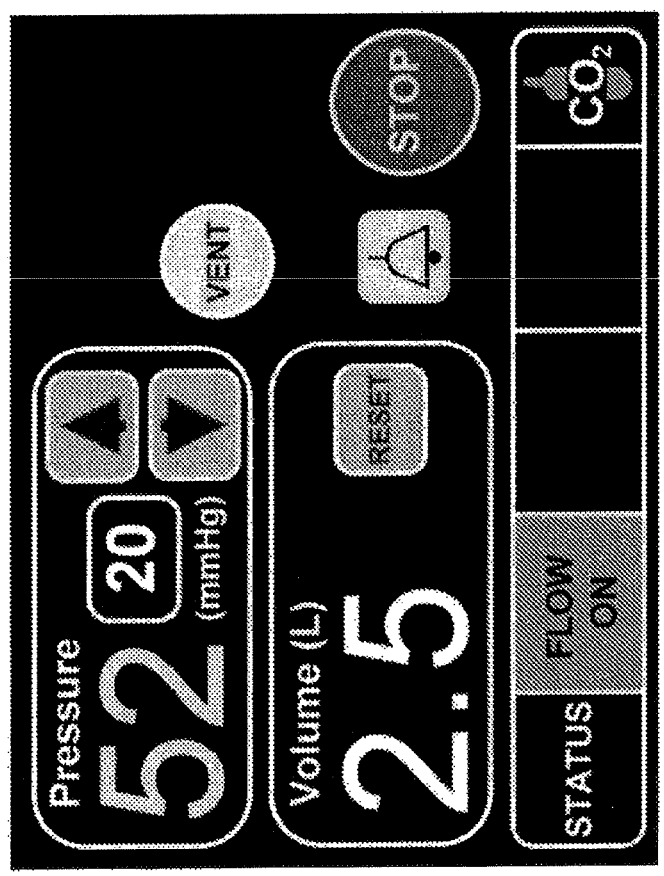
FIG. 12 illustrates a user interface of an insufflating system according to another embodiment of the present invention.
Figure 13:
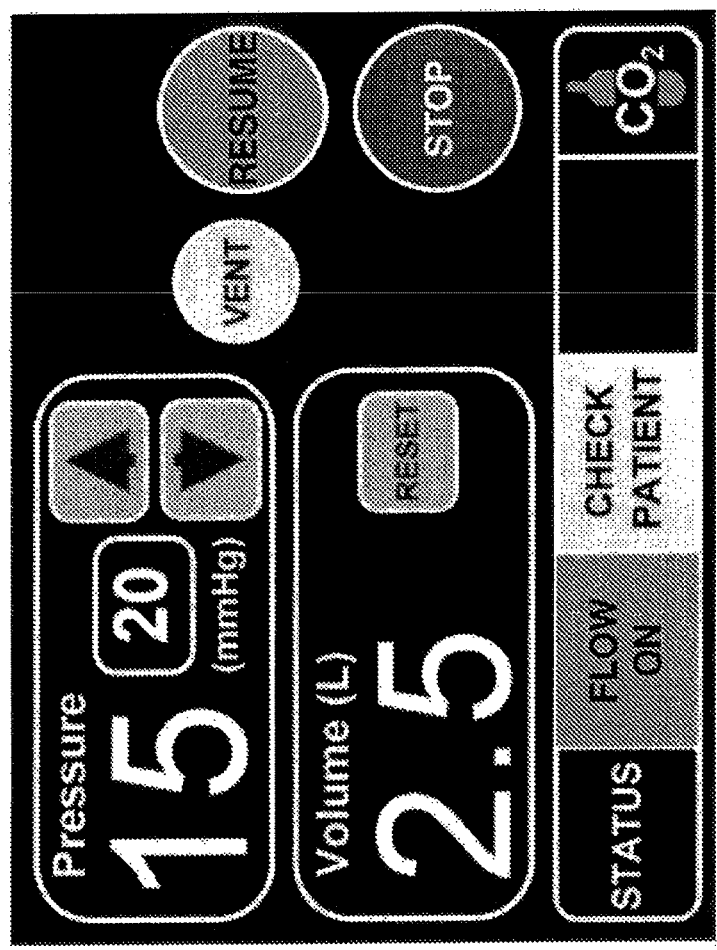
FIG. 13 illustrates a user interface of an insufflating system according to one embodiment of the present invention.

The user interface 200 and/or controller 101 of the insufflating system 100 may, in some embodiments, provide additional functional features. For example, the insufflating system may be configured, in some embodiments, to display the current pressure and update the pressure on the display during the procedure as shown in FIGS. 11-13. In addition, the insufflating system may also be configured to audibly and visually alert the operator if a pressure exceeds a specific threshold for a specific period of time. In one embodiment, the insufflating system 100 may be configured to display an alarm alert 253 on the touch screen of the user interface 200 if the pressure within one of the lumens exceeds a second specified threshold. For example, the user interface may audibly alert and display the alarm alert 253 if the pressure exceeds 50 mmHg for a duration equal to or longer than 5 seconds. Further, the numerals indicating the current pressure, displayed in the pressure display 201, may change colors to further alert the operator, as shown in FIG. 12. The operator may mute the audible alarm by pressing the alarm alert button 253.

As mentioned previously, the volume display 210 provides the operator with information relating to the amount of distending media delivered to the patient. FIGS. 11-13 show that the current volume may be displayed and updated during the procedure. Once the volume of distending media dispensed to the patient equals a preset volume threshold, as defined by the operator's selection in the insufflating system's 100 menu, the status bar of the user interface 200 indicates within a status portion that the flow from the valve assembly 103 to the administration set 150 has been paused or otherwise ceased. In one embodiment, the flow status, as displayed within a status portion of the status bar, may change colors to provide the operator with additional visual indicators that the flow of distending media has been paused. In one embodiment, the user interface 200 may display a flow extend button 254. The flow extend button 254 may be configured to communicate with the controller 101 and the valve assembly 103 to resume flow of the distending media to the administration set until the additional volume of distending media delivered equals a second operator-selected extension volume. Like the preset volume threshold, the second extension volume may be selected by the operator using the user interface 200, as explained in further detail below.

In another embodiment of the present invention, the user interface 200 may be configured to display a vent button 255 upon initiation of the procedure (see FIGS. 11-13). The user interface 200 may be configured to display the vent button 255 at any time during the operation of the insufflating system 100. The vent button 255, displayed on the touch screen of the user interface 200, may be configured to communicate with the controller and a relief valve assembly (not shown). Specifically, once the operator has engaged the vent button 255, the controller engages the relief valve assembly to vent the distending media located within the insufflating system 100, the administration set 150, and/or the organ of the patient to the outside environment. Accordingly, the pressure within the lumens of the administration set 150 will decrease to 0 mmHg. Further, the pressure display 202 will illustrate the current pressure within the lumens of the administration set decreasing to 0 mmHg. In addition, once an operator engages the vent button 255, the status bar 220 may display a vent status within one of the status portions that indicates the relief valve assembly is open and that the distending media is being vented from the insufflating system to the outside environment.

Figure 3:
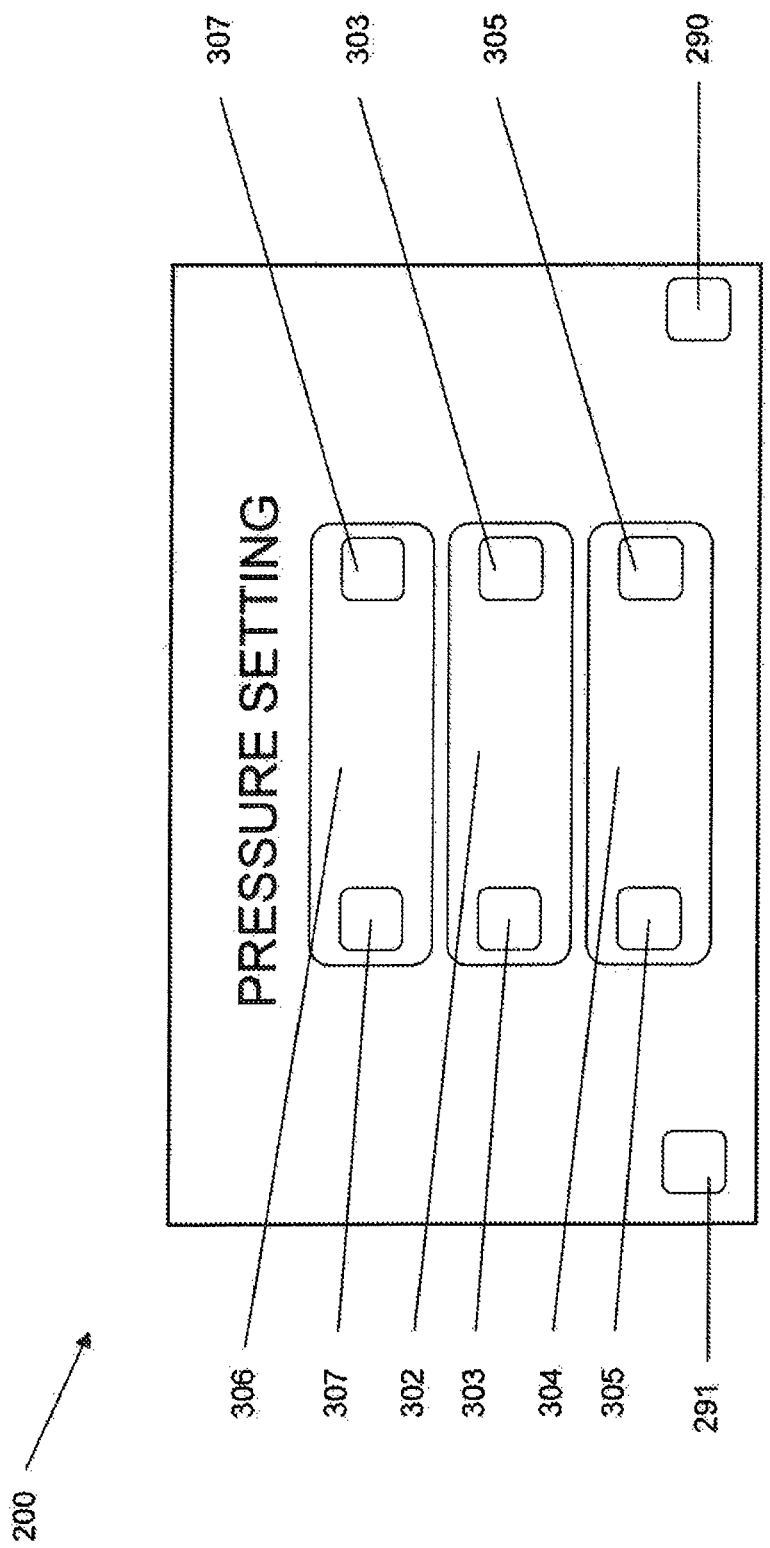
FIG. 3 illustrates a user interface of an insufflating system configured to allow a user to selectively input a desired target pressure according to one embodiment of the present invention.

As mentioned above, according to some embodiments of the present invention, the user interface 200 may be capable of receiving a user input comprising a desired first target insufflation pressure 302 and a final target insufflation pressure 304, as shown in FIG. 3. Specifically, an operator may adjust the desired first target insufflation pressure 302 and final target insufflation pressure 304 by engaging the desired insufflation pressure adjustment buttons 303, 305 prior to commencing flow of the distending media. According to another embodiment, the operator may selectively engage the user interface 200 to activate the first target insufflation pressure threshold by engaging the activation buttons 307. In one embodiment, the operator may deactivate the first target insufflation pressure threshold and the user interface 200 may be configured to display whether the first target insufflation pressure threshold is activated with an indicator 306. If the first target insufflation pressure threshold is deactivated, insufflation will proceed until the final target insufflation pressure threshold is reached without pause. When the insufflating system has commenced flow of the distending media to the organ of the patient, the user interface 200, as shown in FIG. 2, may display the predetermined final target desired insufflation pressure in the selected pressure display 202.

Figure 4:
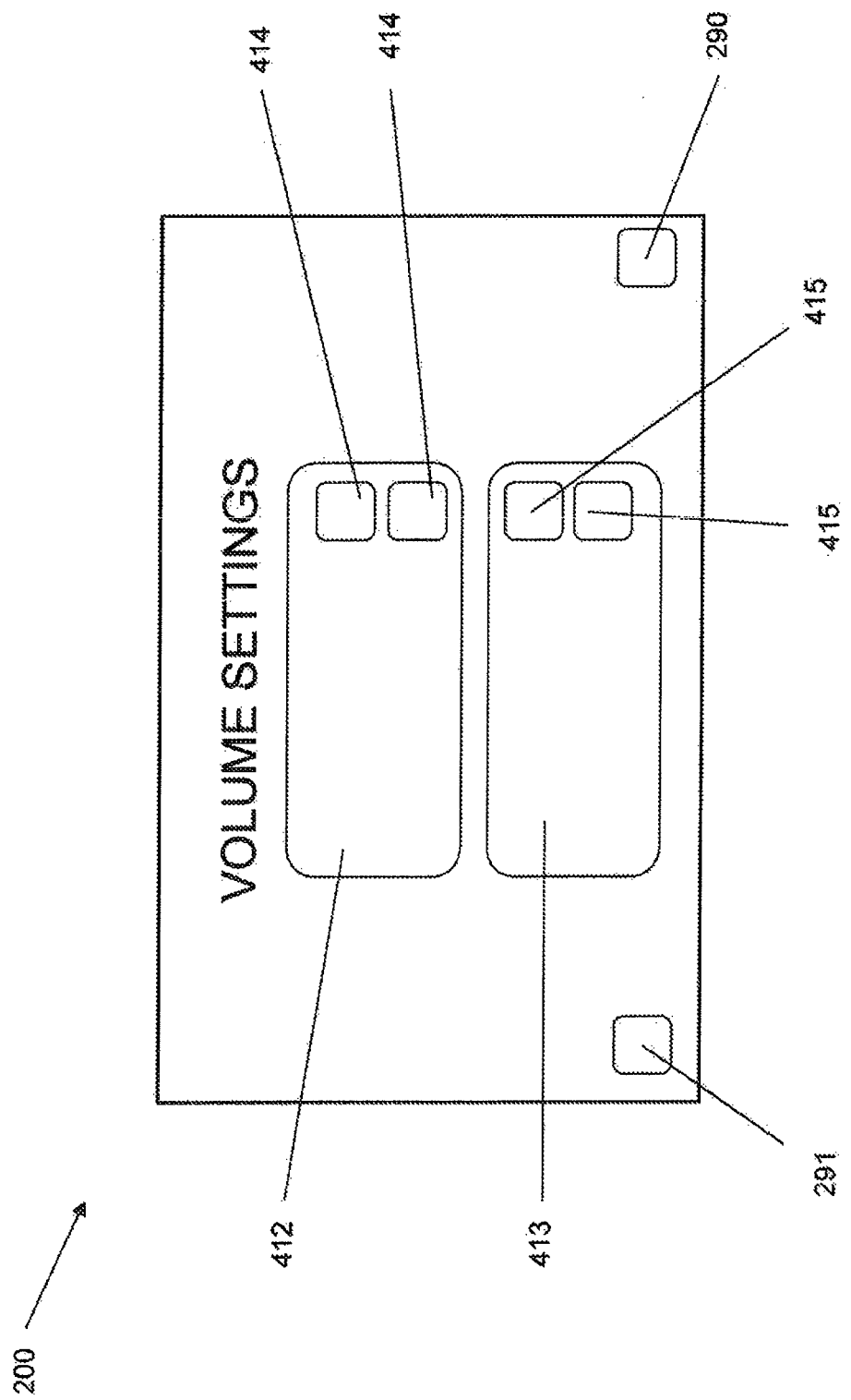
FIG. 4 illustrates a user interface of an insufflating system configured to allow a user to selectively input a desired target volume according to one embodiment of the present invention.

Further, according to another embodiment, the user interface 200 may be capable of receiving a user input comprising a one or more desired volume settings, such as at least one initial flow pause volume level 412 and a second flow extension volume level 413, as shown in FIG. 4. Specifically, an operator may, prior to insufflation of the organ, adjust and select a desired flow pause volume level 412 by engaging the flow pause volume level adjusting buttons 414. Likewise, the operator may adjust and select a desired flow extension volume level 413 by engaging the flow extension volume level adjusting buttons 415. In one embodiment, an operator may selectively adjust the initial flow pause volume level to a value within a range of about 3 to 10 liters and selectively adjust the flow extension volume level to a value within a range of about 1 to 4 liters.

Figure 10:
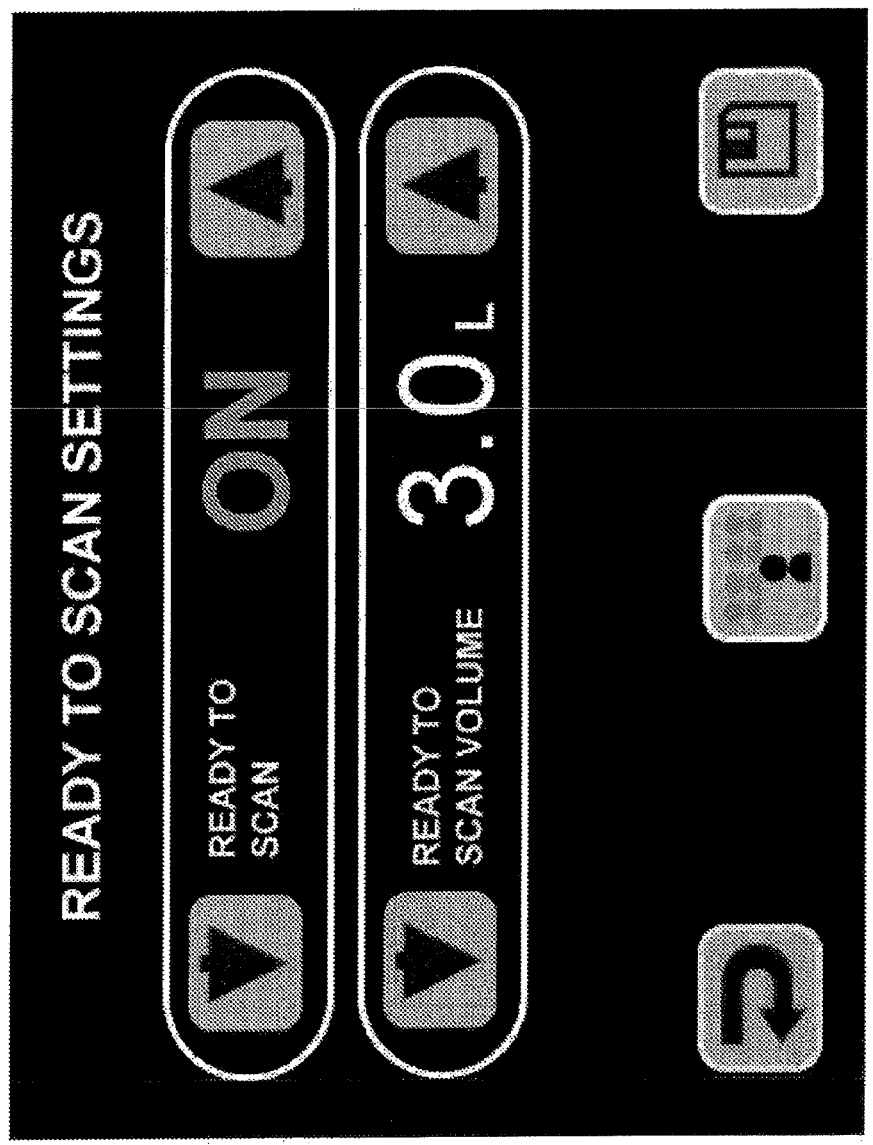
FIG. 10 illustrates a user interface of an insufflating system configured to allow a user to selectively input a desired target volume according to one embodiment of the present invention.

Further still, according to another embodiment, the user interface 200 may be capable of receiving a user input comprising a desired ready to scan volume setting, as shown in FIG. 10. Specifically, an operator may, prior to insufflation of the organ, adjust and select a desired ready to scan volume level by engaging the ready to scan volume level adjusting buttons. In one embodiment, an operator may selectively adjust the ready to scan volume level to a value within a range of about 2 to 5 liters, in increments of about 0.1 liters. In addition, in another embodiment, an operator may selectively disengage the "ready to scan" function by engaging the "ready to scan" operation buttons.

Figure 7:
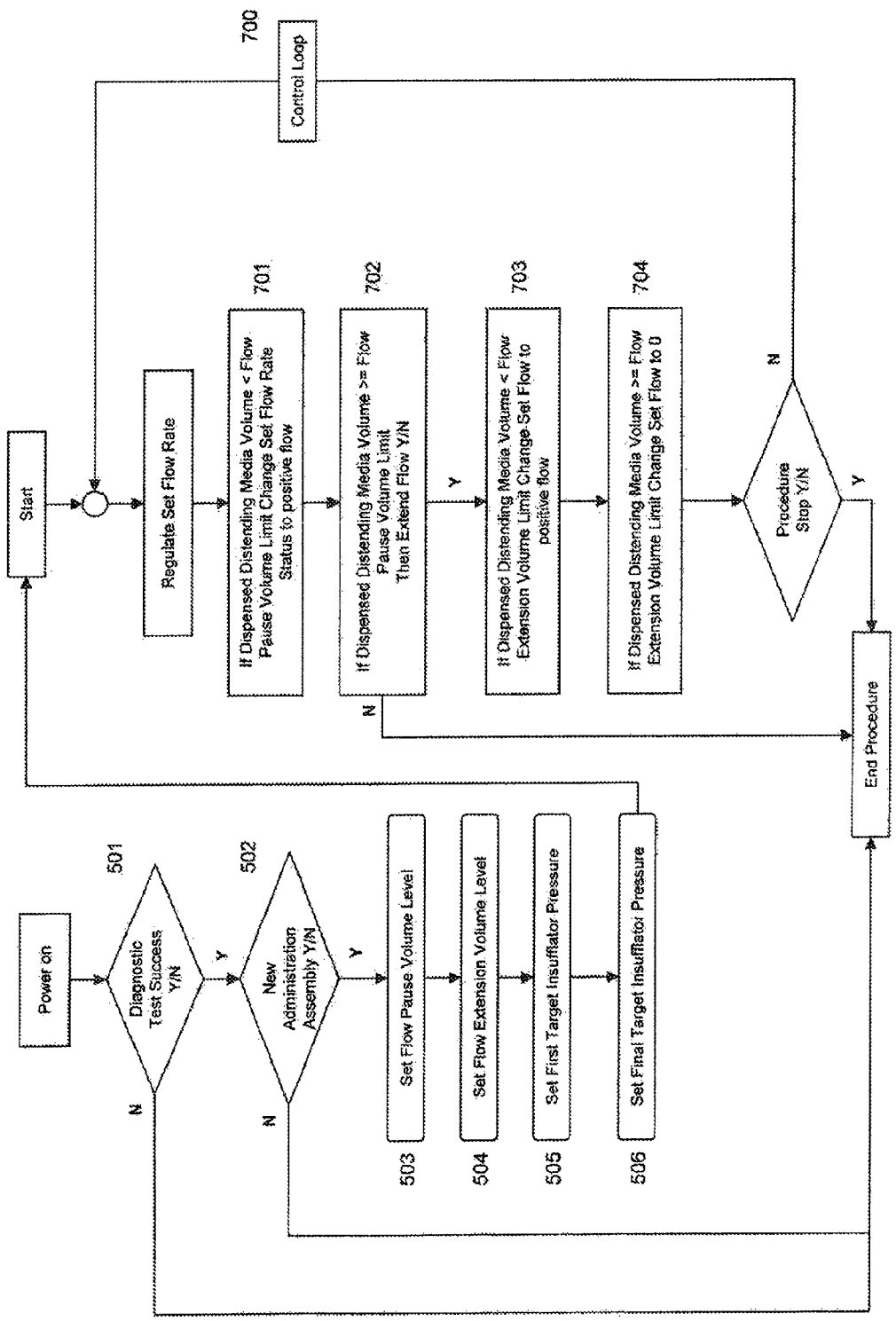
FIG. 7 illustrates a method of providing distending media to an organ of a patient with an insufflating device configured to pause the flow of the distending media according to one embodiment of the present invention.

In some embodiments, the system 100 may further comprise a memory device (not shown) for storing an initial flow pause volume level 412 and a second extending volume level 413 such that the controller 101 may control the valve assembly 103 to pause the flow if the detected volume of distending media dispensed to the administration set 150 exceeds the specified initial flow pause volume level 412. If an operator opts to extend the volume to the second extending volume level, the controller 101 may control the valve assembly 103 to unpause the flow rate and resume dispensing distending media to the administration set until the controller 101 detects the volume of the distending media dispensed is equal to or greater than the second flow extension volume level, as shown in the flow chart illustrated in FIG. 7. For example, an operator may specify and set the initial flow pause volume level 503 to equal about 4 liters and the second flow extension volume level 504 to equal about 2 liters by engaging the flow pause volume level adjusting buttons 414 and the flow extension volume level adjusting buttons 415 respectively, as shown in FIG. 4. The controller may be configured to dispense the distending media to an organ of the patient until the volume of distending media dispensed exceeds a first initial flow pause volume level 701. Further, the controller may be configured to pause the flow if the volume of distending media dispensed equals or exceeds the flow pause volume level 702. If the operator desires to extend the flow, the controller may be further configured to resume the flow of distending media until the volume of distending media dispensed exceeds a second flow extension volume level 703. In addition, the controller may be configured to stop the flow of distending media once the volume of distending media dispensed exceeds the second flow extension volume level 704. According to one embodiment, once the controller 101 detects the amount of distending media dispensed to the patient equals or is greater than about 4 liters, the controller 101 will engage the valve assembly 103 to pause the flow 702. The operator may then select to resume flow of the distending media, and the controller will engage the valve assembly accordingly 703. Once the controller 101 detects that about an additional 2 liters of distending media has been supplied to the administration set 150, the controller will engage the valve assembly 103 to stop the flow of distending media 704. In another embodiment, the user interface 200 may visually or audibly indicate to an operator that the volume of distending media dispensed to the organ of the patient is approaching the flow pause volume level and may be further configured to allow an operator to continue the flow of distending media so that the insufflating system provides an additional predetermined volume of distending media to the organ of a patient. Specifically, the user interface may alert the user and display the flow extend button prior to the controller detecting the volume of distending media dispensed equals the specified initial flow pause volume level. The controller may be configured to signal the user interface to alert the operator that the volume of distending media dispensed to the organ of the patient is equal to a predetermined percentage of the flow pause volume level.

Therefore, embodiments of the present invention may provide several advantages. For example, one embodiment of the present invention provides an operator with a wireless remote to operate the insufflating system from a location removed from the medical imaging device during CT colonography procedures. Thus, the wireless remote advantageously limits the amount of radiation exposure the operator may be subjected to during CT colonography procedures. Further, another embodiment provides an insufflating device comprising a visual indicator configured to quickly inform the operator to initiate a scan with a medical imaging device in order to perform a CT colonography. Specifically, the "ready-to-scan" feature advantageously allows an operator to initiate a scan without having to calculate whether a scan is appropriate from data visible on the face of an insufflating device. Thus, one advantageous aspect of an embodiment of the present invention is providing an operator with a clear and accurate indicator which may streamline the CT colonography or other procedure. Moreover, embodiments of the present invention may provide additional safeguards to the patient as well as ensure patient comfort during the procedure by implementing predetermined pressure and volume thresholds and insuring that the proper administration set is used and is used only once.

Other modifications and other embodiments of the invention set forth herein will come to mind to one skilled in the art to which this invention pertains having the benefit of the teachings presented in the foregoing descriptions and on the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Further, throughout the description, where compositions are described as having, including, or comprising specific components, or where processes systems or methods are described as having, including, or comprising specific steps, it is contemplated that compositions or the present invention may also consist essentially or, or consist of the recited components, and that the processes or methods of the present invention also consist essentially or consist of the recited steps. Further, it should be understood that the order of steps or order of performing certain actions are immaterial so long as the invention remains operable. Moreover, two or more steps or actions may be conducted simultaneously with respect to the invention disclosed herein.

That which is claimed is:

1. An insufflating system adapted to be in fluid communication with a source of a distending media for delivering the distending media to a patient's colon for acquiring an image of the colon while distended, the insufflating system comprising:
   an insufflating device comprising:

a controller configured for detecting a plurality of different preset pressure levels of the distending media within the colon of the patient; and a valve assembly in communication with the controller and in fluid communication between the source of distending media and the colon of the patient, wherein the valve assembly is configured to adjust a flow rate of the distending media flowing out of the insufflating device and delivered to the colon of the patient in response to a signal provided by the controller, wherein the controller is configured to close the valve assembly of the insufflating device to pause further delivery of the distending media from the insufflating device to the colon in response to detecting any one of the preset pressure levels of the distending media delivered to the colon, thereby allowing an operator to check a distention of the patient's colon, and wherein the controller is further configured to open the valve assembly of the insufflating device to resume delivery of the distending media from the insufflating device to the colon in response to a selection from the operator, except when a final target insufflation pressure level is detected, such that a maximum volume of distending media in a distended portion of the colon for safety or comfort of the patient is not exceeded; and wherein the controller is further configured such that, after first detecting the final target insufflation pressure level, the controller controls the valve assembly to regulate a flow of the distending media and thereby maintains a pressure of the distending media within the colon of the patient within a range of +/−10% with respect to the final target insufflation pressure level.

2. The insufflating system according to claim 1, further comprising a user interface in communication with the controller and configured to signal the operator of the insufflating system that proper insufflation has been achieved for acquiring an image of the colon of the patient.

3. The insufflating system according to claim 1, wherein the controller is configured to provide an indication that proper distension has been achieved for acquiring an image of the colon of the patient using computer tomography.

4. The insufflating system according to claim 1, wherein the controller is configured to, after detecting the final target insufflation pressure level, monitor a pressure level of the distending media within the colon of the patient and to provide an indication that proper distension has been achieved for acquiring an image of the colon based on the monitored pressure level being within a predetermined pressure range for a predetermined period of time.

5. The insufflating system according to claim 4, wherein the controller is further configured to detect at least one predetermined volume level of the distending media delivered to the colon, and wherein the controller is configured to provide an indication that proper distension has been achieved for acquiring an image of the colon of the patient based on the detected pressure level being within a predetermined pressure range for the predetermined period of time and the at least one detected volume level.

6. The insufflating system according to claim 1, further comprising a relief valve in communication with the controller, wherein the controller is further configured to actuate the relief valve in order to vent the distending media from the colon.

7. The insufflating system according to claim 1, further comprising a wireless remote configured to communicate with the controller for controlling operation thereof.

8. The insufflating system according to claim 1, further comprising a relief valve assembly in communication with the controller, wherein the relief valve assembly is configured to vent the distending media in response to detecting a predetermined pressure threshold for a predetermined period of time.

9. The insufflating system according to claim 1, wherein the controller is further configured to detect at least one predetermined volume level of the distending media within the colon of the patient.

10. The insufflating system according to claim 9, wherein the controller is configured to close the valve assembly to pause further delivery of the distending media in response to detecting a first predetermined volume level of the distending media delivered to the colon.

11. The insufflating system according to claim 10, wherein the controller is further configured to open the valve assembly to resume delivery of the distending media in response to a selection and close the valve assembly in response to detecting a second predetermined volume level.

12. The insufflating system according to claim 1, wherein the valve assembly is further configured to provide a first flow rate while a first volume of distending media is delivered, a second flow rate while a second volume of distending media is delivered, and a third flow rate after the second volume of distending media is delivered.

13. The insufflating system according to claim 1, further comprising an administration set configured to be in fluid communication with the insufflating device and to direct the distending media from the valve assembly to the colon of the patient.

14. The insufflating system according to claim 13, wherein the administration set comprises a security assembly configured to facilitate a connection between the administration set and the insufflating device.

15. The insufflating system according to claim 14, wherein the security assembly is configured to allow a connection between the administration set and the insufflating device when the security assembly detects that the administration set has not been previously used or that the security assembly is compatible with the insufflating device.

16. The insufflating system according to claim 1, wherein the selection from the operator comprises selection of a button on a user interface configured to resume flow of the distending media.

17. A method for delivering distending media to a patient's colon with a dispensing device for acquiring an image of the colon while distended, the method comprising:

delivering, via a controller of an insufflating device, the distending media from the insufflating device to the colon of the patient;

pausing, via the controller, delivery of the distending media from the insufflating device in response to detecting a first preset pressure level of the distending media delivered to the colon in order to allow an operator of an insufflating system comprising the insufflating device to check a status of the patient;

resuming, via the controller, delivery of the distending media from the insufflating device to the colon in response to a selection by the operator;

ceasing, via the controller, delivery of the distending media from the insufflating device to the colon in response to detecting a final target insufflation pressure level, wherein the final target insufflation pressure level is different than the first preset pressure level, such that a maximum volume of distending media in a distended portion of the colon for safety or comfort of the patient is not exceeded; and regulating, via the controller, a flow of the distending media and thereby maintaining a pressure of the distending media within the colon of the patient within a range of +/−10% with respect to the final target insufflation pressure level after first detecting the final target insufflation pressure level.

18. The method according to claim 17, further comprising:

detecting a pressure level of the distending media within the colon of the patient; and providing an indication that proper distension has been achieved for acquiring an image of the colon of the patient based at least on the pressure level being within a predetermined pressure range for a predetermined period of time.

19. The method according to claim 18, further comprising detecting at least one predetermined volume level of the distending media delivered to the colon, wherein the providing step comprises providing an indication that proper distension has been achieved for acquiring an image of the colon of the patient based on the pressure level being within the predetermined pressure range for the predetermined period of time and the at least one detected volume level.

20. The method according to claim 17, wherein the selection from the operator comprises selection of a button on a user interface configured to resume flow of the distending media.

21. A method for delivering distending media to a patient's colon with a dispensing device for acquiring an image of the colon while distended, the method comprising:

delivering, via a controller of an insufflating device, the distending media from the insufflating device to the colon of the patient;

pausing, via the controller, delivery of the distending media from the insufflating device in response to detecting a first preset pressure level of the distending media delivered to the colon in order to allow an operator of an insufflating system comprising the insufflating device to check a status of the patient;

resuming, via the controller, delivery of the distending media from the insufflating device to the colon in response to a selection by the operator;

ceasing, via the controller, delivery of the distending media from the insufflating device to the colon in response to detecting a second preset pressure level, wherein the second preset pressure level is different than the first preset pressure level;

after detecting a final target insufflation pressure level, monitoring, via the controller, a pressure level of the distending media within the colon of the patient and providing an indication that proper distension has been achieved for acquiring an image of the colon based on the monitored pressure level being within a predetermined pressure range for a predetermined period of time; and regulating, via the controller, a flow of the distending media and thereby maintaining the pressure level of the distending media within the colon of the patient within a range of +/−10% with respect to the final target insufflation pressure level after first detecting the final target insufflation pressure level.

22. The method according to claim 21, wherein the selection from the operator comprises selection of a button on a user interface configured to resume flow of the distending media.

\* \* \* \* \*